(12) United States Patent
Portoghese et al.

(10) Patent No.: US 6,500,824 B1
(45) Date of Patent: Dec. 31, 2002

(54) KAPPA (OP$_2$) OPIOID RECEPTOR ANTAGONISTS

(75) Inventors: Philip S. Portoghese, St. Paul, MN (US); Robert M. Jones, Salt Lake City, UT (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/762,418

(22) PCT Filed: Aug. 6, 1999

(86) PCT No.: PCT/US99/18021

§ 371 (c)(1),
(2), (4) Date: Feb. 6, 2001

(87) PCT Pub. No.: WO00/08027

PCT Pub. Date: Feb. 17, 2000

Related U.S. Application Data

(60) Provisional application No. 60/095,514, filed on Aug. 6, 1998.

(51) Int. Cl.[7] .................. A61K 31/535; A61K 31/44; C07P 413/00; C07P 221/22

(52) U.S. Cl. .................. 514/232.8; 514/279; 544/125; 546/35

(58) Field of Search .................. 546/35; 514/279, 514/232.8; 544/125

(56) References Cited

U.S. PATENT DOCUMENTS 5,578,725 A * 11/1996 Portoghese et al. ........... 546/35
5,886,001 A * 3/1999 Schmidhammer et al. .. 514/279

OTHER PUBLICATIONS

Linner, K.M., et al., "The $\delta_1$–opioid receptor antagonist, 7–benzylspiroindanylnaltrexone, prolongs renal allograft survival in a rat model", *European Journal of Pharmacology, 354*, pp. R3–R5, (1998).

* cited by examiner

*Primary Examiner*—Alan L. Rotman
*Assistant Examiner*—Raymond Covington

(57) ABSTRACT

The invention provides kappa receptor antagonists of formula (I), wherein $R_1$–$R_6$ X and Y have any of the meanings given in the specification, as well as compositions comprising them, and methods for their use.

22 Claims, 7 Drawing Sheets

KAPPA (OP₂) OPIOID RECEPTOR ANTAGONISTS

This application claims the benefit of provisional application No. 60/095,514, filed Aug. 6, 1998.

GOVERNMENT FUNDING

This invention was made with government support awarded by National Institutes of Health #da01533. The Government has certain rights in this invention.

BACKGROUND OF THE INVENTION

Endogenous opioid peptides are involved in the mediation or modulation of a variety of mammalian physiological processes, many of which are mimicked by opiates or other non-endogenous opioid ligands. Some of the effects that have been suggested include analgesia, tolerance and dependence, appetite, renal function, gastrointestinal motility, gastric secretion, learning and memory, mental illness, epileptic seizures and other neurological disorders, cardiovascular responses, and respiratory depression (see G. T. Shearman et al. *J. Pharmacol. Exp. Ther.*, 243, 591–597, 1987).

The fact that the effects of endogenous and exogenous opioids are mediated by at least three different types of opioid receptors raises the possibility that highly selective exogenous opioid agonist or antagonist ligands might have therapeutic applications. Thus, if a ligand acts at a single opioid receptor type or subtype, the potential side effects mediated through other opioid receptor types can be minimized or eliminated.

The selectivities of the prototypical delta (naltrindole, U.S. Pat. No. 4,816,586) and kappa (norbinaltorphimine, nor-BNI, U.S. Pat. No. 4,649,200) opioid antagonists have been attributed to the presence of non-peptide "address mimics" which bear a functional relationship to key motifs in the putative delta and kappa addresses of the endogenous opioid peptides, dynorphin-A and enkephalin, respectively. P. S. Portoghese et al. *J. Med. Chem.* 1993, 36, 179–180 and U.S. Pat. No. 5,457,208 reported a series of NTI analogues in which the C5' position of the indolic benzenoid ring is substituted with an alkyl amidine pendant.

Currently a need exists for kappa receptor antagonists that can be used as therapeutic agents, or as pharmacological tools to further investigate kappa receptor binding, structure, and function.

SUMMARY OF THE INVENTION

The invention provides a series of kappa antagonists, which demonstrate highly selective pharmacological antagonism both in vivo and in vitro at the kappa opioid receptor.

Accordingly there is provided a compound of the invention which is a compound of formula (I):

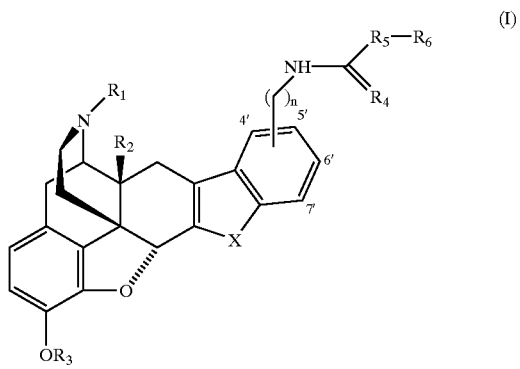

wherein

R₁ is $(C_1-C_6)$alkyl, $(C_2-C_6)$alkenyl, $(C_2-C_6)$alkynyl, $(C_3-C_7)$cycloalkyl, $(C_5-C_7)$cycloalkenyl, $(C_3-C_6)$cycloalkyl$(C_1-C_6)$alkyl, $(C_5-C_7)$cycloalkenyl$(C_1-C_6)$alkyl, aryl, heteroaryl, aryl$(C_1-C_6)$alkyl, or heteroaryl$(C_1-C_6)$alkyl;

R₂ is H, OH, $(C_1-C_6)$alkoxy, $(C_1-C_6)$alkanoyloxy, $NR_aR_b$ or $SR_c$;

R₃ is H, aryl$(C_1-C_6)$alkyl, $(C_1-C_6)$alkyl, $(C_1-C_6)$alkanoyl, or $(C_1-C_6)$alkylC(=S);

is $R_4$ is =O, =S, or =$NR_d$;

$R_d$ is H, CN, $CONH_2$, $COCF_3$, $(C_1-C_6)$alkanoyl, $(C_1-C_6)$alkyl, or $(CH_2)_pNR_eR_f$; or $R_d$ together with $R_6$ is —$(CH_2)_q$— and forms a ring;

p is 1,2,3, or 4;

R₅ is $NR_m$;

R₆ is H, $(C_1-C_6)$alkyl, $(C_3-C_7)$cycloalkyl, aryl, heteroaryl, aryl$(C_1-C_6)$alkyl, heteroaryl$(C_1-C_6)$alkyl, $NR_gR_h(C_1-C_6)$alkyl, or $C(=NR_j)NHR_k$; or when $R_4$ is =$NR_d$, $R_6$ together with $R_d$ is —$(CH_2)_q$— and forms a ring;

q is 2 or 3;

X is O, S, or NY;

Y is H, $(C_1-C_6)$alkyl, or aryl$(C_1-C_6)$alkyl;

n is 0, 1, 2, 3, or 4;

$R_a$—$R_c$ and $R_e$—$R_f$ are each independently H, $(C_1-C_6)$alkyl, $(C_1-C_6)$alkanoyl, or —C(=S)$(C_1-C_6)$alkyl;

$R_g$ and $R_h$ are each independently H, $(C_1-C_6)$alkyl, $(C_1-C_6)$alkanoyl, —C(=NH)$NR_aR_b$, or —C(=S)$(C_1-C_6)$alkyl, or $R_g$ and $R_h$ together with the nitrogen to which they are attached are pyrrolidino, piperidino or morpholino;

$R_j$ and $R_k$ are each independently H, $(C_1-C_6)$alkyl, $(C_2-C_6)$alkenyl, $(C_2-C_6)$alkynyl, $(C_3-C_7)$cycloalkyl, $(C_3-C_7)$cycloalkyl$(C_1-C_6)$alkyl, $(C_5-C_7)$cycloalkenylalkyl, aryl, heteroaryl, aryl$(C_1-C_6)$alkyl, or heteroaryl$(C_1-C_6)$alkyl; and $R_m$ is hydrogen or $(C_1-C_6)$alkyl;

or a pharmaceutically acceptable salt thereof;

The invention also provides a pharmaceutical composition comprising a compound of formula I, or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein kappa receptor activity is implicated and antagonism of kappa receptors is desired comprising administering to the mammal, an effective amount of a compound of formula I, or a pharmaceutically acceptable salt thereof.

The invention provides a compound of formula I for use in medical therapy (preferably for use in treating conditions wherein antagonism of kappa receptors is indicated, e.g. for appetite suppression, as an antipsychotic, or to treat paralysis due to ischemic spinal cord injury), as well as the use of a compound of formula I for the manufacture of a medicament for the treatment of a pathological condition or symptom in a mammal, such as a human, wherein antagonism of kappa receptors is indicated.

The invention also includes a method for binding a compound of formula I to kappa receptors, in vivo or in vitro, comprising contacting mammalian tissue comprising said receptors with an amount of a compound of formula I effective to bind to said receptors. Tissue comprising ligand bound kappa receptors is useful to measure the receptor selectivity of other potential therapeutic agents, or can be used as a tool to identify potential therapeutic agents for the treatment of diseases or conditions wherein kappa receptor activity is implicated and antagonism of kappa receptors is desired, by contacting said agents with said ligand-receptor complexes, and measuring the extent of displacement of the ligand and/or binding of the agent (for example in a competitive binding assay).

DETAILED DESCRIPTION

Figure 1:
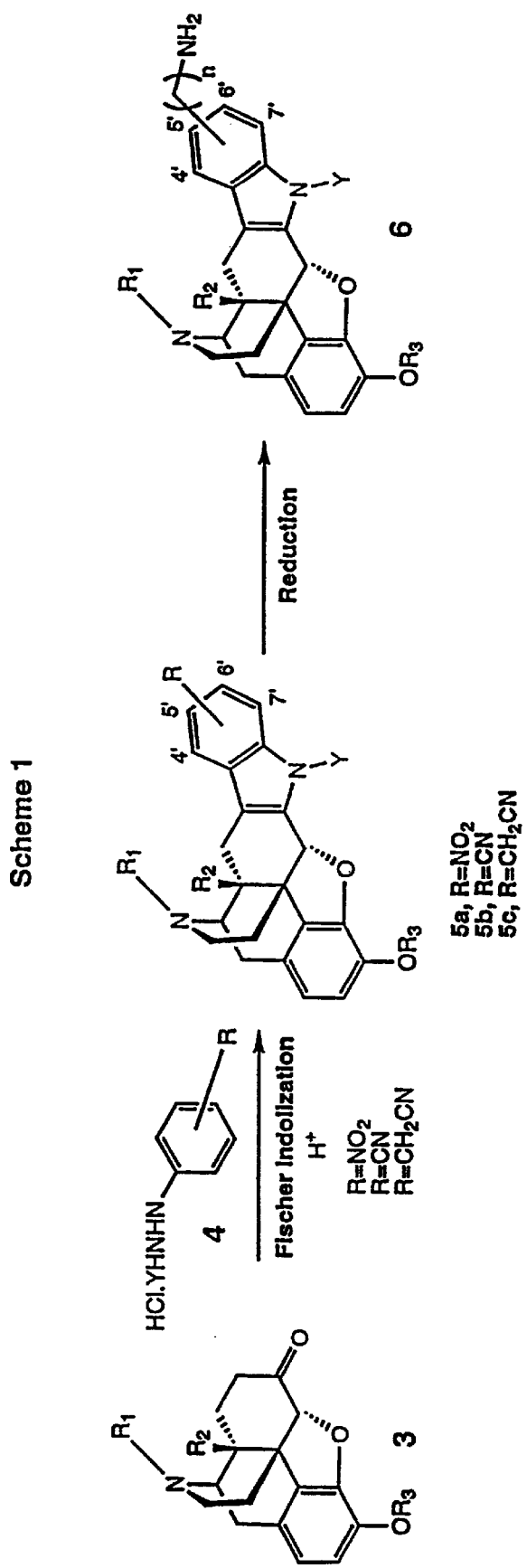
FIG. 1 Illustrates the synthesis of an intermediate of formula 6.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine kappa antagonist activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_7)$cycloalkyl can be cyclopropyl, cyclobutyl, cyclopentyl, cyclohexyl, or cycloheptyl; $(C_3-C_7)$cycloalkyl $(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$ alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; and $(C_2-C_6)$ alkanoyloxy can be acetoxy, propanoyloxy, butanoyloxy, isobutanoyloxy, pentanoyloxy, or hexanoyloxy; aryl can be phenyl, indenyl, or naphthyl; heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, $R_1$ is $(C_2-C_6)$alkenyl or $(C_3-C_6)$cycloalkyl $(C_1-C_6)$alkyl. More specifically, $R_1$ is cyclopropylmnethyl or allyl.

Specifically, $R_2$ is OH.

Specifically, $R_3$ is H.

Specifically, $R_4$ is $=NR_d$. More specifically, $R_4$ is =NH or =NCN.

Specifically, $R_5$ is NH.

Specifically, $R_6$ is hydrogen, ethyl, n-butyl, 3-(dimethylamino)-propyl, or 2-pyrrolidinoethyl. More specifically, $R_6$ is H. Another specific $R_6$ is C(=N$_j$)NHR$_k$.

Specifically, $R_m$ is hydrogen.
Specifically, n is 0.
Specifically, n is 1.
Specifically, the group

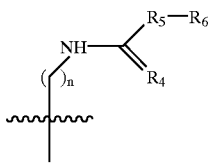

is substituted at the 5' position of the formula (I) ring system.
Specifically, X is NH.
A specific compound of the present invention is a compound of formula (I):

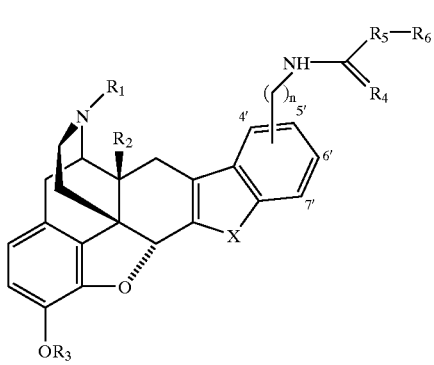

(I)

wherein:
- $R_1$ is $(C_1-C_6)$alkyl, $(C_2-C_6)$alkenyl, $(C_2-C_6)$alkynyl, $(C_3-C_7)$cycloalkyl, $(C_5-C_7)$cycloalkenyl, $(C_3-C_6)$cycloalkyl$(C_1-C_6)$alkyl, $(C_5-C_7)$cycloalkenyl$(C_1-C_6)$alkyl, aryl, heteroaryl, aryl$(C_1-C_6)$alkyl, heteroaryl$(C_1-C_6)$alkyl;
- $R_2$ is H, OH, $(C_1-C_6)$alkoxy, $(C_1-C_6)$alkanoyloxy, $NR_aR_b$, or $SR_c$
- $R_3$ is H, aryl$(C_1-C_6)$alkyl, $(C_1-C_6)$alkyl, $(C_1-C_6)$alkanoyl, or $(C_1-C_6)$alkylC(=S).
- $R_4$ is =O, =S, =$NR_d$, wherein $R_d$ is H, CN, $CONH_2$, $COCF_3$, $(C_1-C_6)$alkanoyl, $(C_1-C_6)$alkyl, or $(CH_2)_p NR_eR_f$, wherein p=1–4;
- $R_5$ is NH;
- $R_6$ is H, $(C_1-C_6)$alkyl, $(C_3-C_7)$cycloalkyl, aryl, heteroaryl, aryl$(C_1-C_6)$alkyl, heteroaryl$(C_1-C_6)$alkyl, $NR_gR_h(C_1-C_6)$alkyl, or $C(=NR_j)NHR_k$; or when $R_4$ is =N, $R_6$ can be —$(CH_2)_q$— and form a ring with the N of $R_4$, wherein q is 2 or 3;
- X is O, S, or NY, wherein Y is H $(C_1-C_6)$alkyl, or aryl$(C_1-C_6)$alkyl;
- n is 0, 1, 2, 3, or 4;
- $R_a-R_f$ are each independently H, $(C_1-C_6)$alkyl, $(C_1-C_6)$alkanoyl, or —C(=S)$(C_1-C_6)$alkyl;
- $R_g$ and $R_h$ are each independently H, $(C_1-C_6)$alkyl, $(C_1-C_6)$alkanoyl, —C(=NH)$NR_aR_b$, or —C(=S)$(C_1-C_6)$alkyl, or $R_g$ and $R_h$ together with the nitrogen to which they are attached are pyrrolidino, piperidino or morpholino; and
- $R_j$ and $R_k$ are each independently H, $(C_1-C_6)$alkyl, $(C_2-C_6)$alkenyl, $(C_2-C_6)$alkynyl, $(C_3-C_7)$cycloalkyl, $(C_3-C_7)$cycloalkyl$(C_1-C_6)$alkyl, $(C_5-C_7)$ cycloalkenylalkyl, aryl, heteroaryl, aryl$(C_1-C_6)$alkyl, or heteroaryl$(C_1-C_6)$alkyl;

or a pharmaceutically acceptable salt thereof.

A specific compound of the invention is a compound of formula I wherein $R_6$ is not $(C_1-C_6)$alkyl when n is 1, $R_4$ is NH, and $R_5$ is NH.

A specific compound of the invention is a compound of formula I wherein $R_d$ together with $R_6$ is —$(CH_2)_q$— and forms a ring.

A specific compound of the present invention is 5'-guanidinyl-17-cyclopropylmethyl-6,7-didehydro-4,5-α-epoxy-3,14-dihydroxyindolo[2',3':6,7]morphinan ditrifluoroacetate dihydrate (15, GNTI).

A specific compound of the present invention is 5'-N-ethylguanidinyl-17-cyclopropylmethyl-6,7-didehydro-4,5-α-epoxy-3,14-dihydroxyindolo[2',3':6,7]morphinan ditrifluoroacetate dihydrate (16).

A specific compound of the present invention is 5'-N-butylguanidinyl-17-cyclopropylmethyl-6,7-didehydro4,5-α-epoxy-3,14-dihydroxyindolo[2',3':6,7]morphinan ditrifluoroacetate dihydrate (17).

A specific compound of the present invention is 5'-N-butylguanidinyl-17-cyclopropylmethyl-6,7-didehydro-4,5-α-epoxy-3,14-dihydroxyindolo[2',3':6,7]morphinan ditrifluoroacetate dihydrate (18).

A specific compound of the present invention is 5'-N'-cyano-N-[17-(cyclopropylmethyl)-6,7-didehydro-4,5α-epoxy-3,14-dihydroxyindolo[2',3':6,7]morphinian]-guanidine (19).

A specific compound of the present invention is 5'-N-cyano-N'-[3-(dimethylaminopropyl)]-N"-[17-(cyclopropylmethyl)-6,7-didehydro-4,5α-epoxy-3,14-dihydroxyindolo[2',3':6,7]morphinian]-guanidine (20).

A specific compound of the present invention is 5'-N-cyano-N'-[2-(1-aminoethylpyrrolidine)]-N"-[17-(cyclopropylmethyl)-6,7-didehydro-4,5α-epoxy-3,14-dihydroxyindolo[2',3':6,7]morphinian]-guanidine (21).

The invention also provides processes and intermediates useful for preparing compounds of formula I such as those described in the Examples or illustrated in the figures herein.

The compounds of general formula I, or salts or solvates thereof, maybe prepared by the methods illustrated in schemes 1–6 (FIGS. 1 and 2), or by modification thereof, using readily available starting materials, reagents and conventional synthetic procedures.

The compounds of general formula I wherein X is NH can be readily synthesized by reaction of a 4,5-epoxy-6-ketomorphinan such as naltrexone (3, $R_1$=cyclopropylmethyl=CPM, $R_2$=OH, $R_3$=H, scheme 1) with a substituted phenyl hydrazine 4 under Fischer indolization conditions (see D. L. Hughes. Org. Prep. Proc. Intl. 25(6), 607–632, 1993). The indolomorphinan products 5 are subsequently reduced to the primary amines 6 by utilizing the reduction conditions set out in FIG. 1 (Scheme 1).

Guanidinyl compounds of general formula 7 (FIG. 2, scheme 2) can be prepared from amines 6 (where n=0-3) by reaction with a modified thiourea derivative 8 using mercuric(II)chloride assisted guanidylation protocols (see K Y. Kim; L. Qian. Tet. Lett. 1993, 34, 48, 7677–7680 and M. A. Poss; E. Iwanowicz; J. A. Reid; J. Lin; Z. Gu. Tet. Lett. 33, 40, 5933–5936, 1992) followed by acid deprotection. 5'-GNTI ($R_1$=cyclopropylmethyl=CPM, $R_2$=OH, $R_3$=H, X=NH, $R_4$=NH, $R_5$=NH, $R_6$=H as its trifluoroacetate salt, general formula I) or more specifically 5'-guanidinyl-17-cyclopropylmethyl-6,7-didehydro-4,5-α-epoxy-3,14-dihydroxyindolo[2',3':6,7]-morphinan ditrifluoroacetate dihydrate is a specific example of this class.

Cyanoguanidines of general formula 10 (FIG. 2, scheme 3) maybe obtained from amines 6 by reaction with diphenyl-N-cyanocarbonimidate 9 (see C. J. Durant et al. *J. Med. Chem.* 1977, 20, 7, 901 and R. L. Webb, C. S. Labaw.*J. Het. Chem.* 19, 1205, 1982) followed by displacement of phenol from the intermediate by reaction with a primary amine or general formula $R_6NH_2$. 5'-CNGNTI ($R_1$= cyclopropylmethyl=CPM, $R_2$=OH, $R_3$=H, X =NH, $R_4$=NCN, $R_5$=NH, $R_6$=H, general formula I) or more specifically 5'-N-cyanoguanidinyl-17-cyclopropylmethyl-6,7-didehydro-4,5-α-epoxy-3,14-dihydroxyindolo[2',3':6,7]-morphinan is a specific example of this class.

Ureas of general formula 11 (FIG. 2, scheme 4) wherein W is O or S can be readily prepared by reaction of amines 6 with $R_6NCW$. Specific variants of the above are cited in reaction scheme 5. Commercially available modified isothiocyanates of general formula 13 (n=0–3) (Fluka) are reacted with amines 6. Deprotection of the terminal tert-BOC moiety followed by guanidylation (see K. Y. Kim; L. Qian. *Tet. Lett.* 1993, 34, 48, 7677–7680 and M. A. Poss; E. Iwanowicz; J. A. Reid; J. Lin; Z. Gu. *Tet. Lett.* 33, 40, 5933–5936, 1992) and a second acid mediated tert-BOC deprotection yields compounds of general formula 12.

Figure 2:
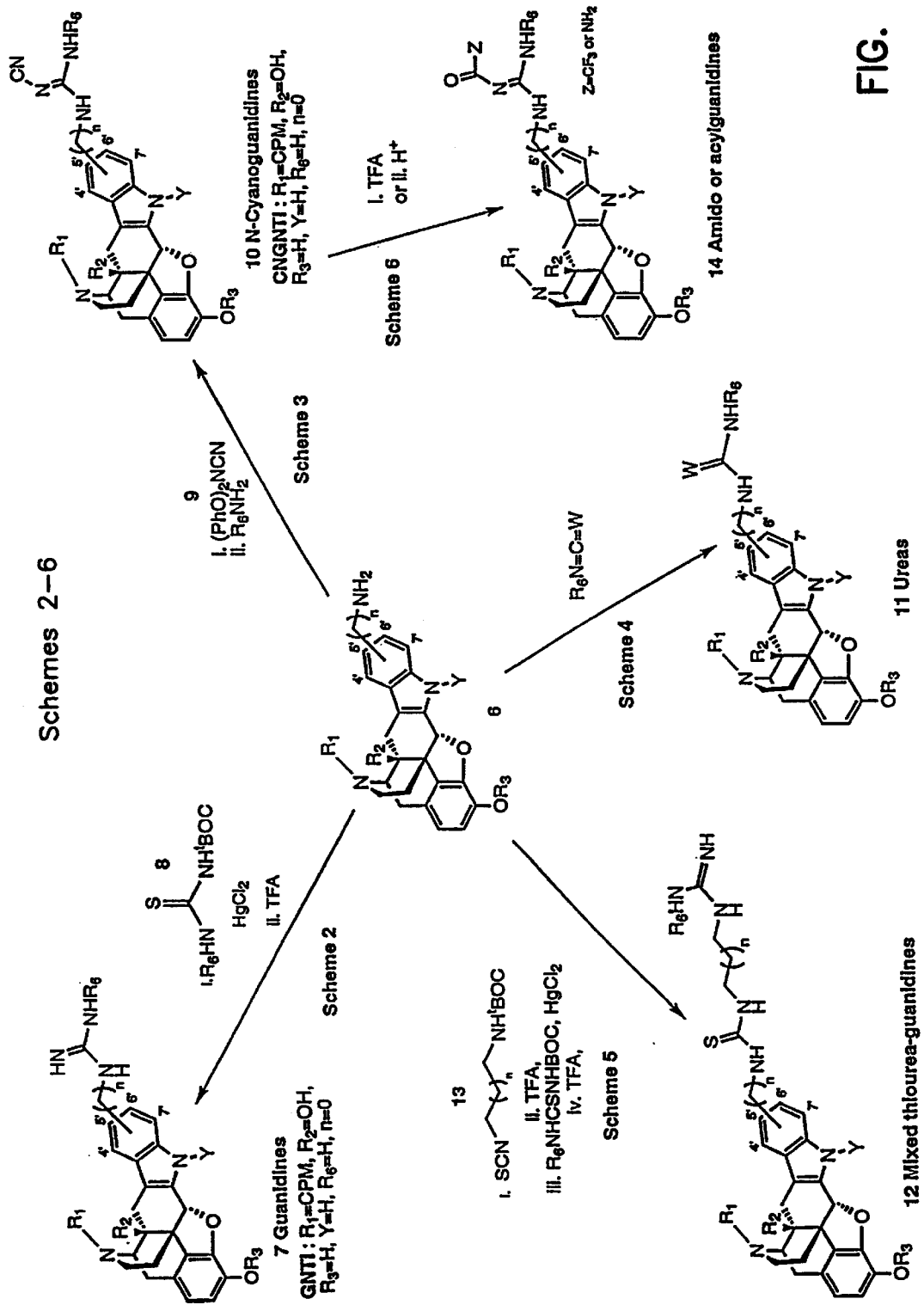
FIG. 2 Illustrates the synthesis of compounds of the invention.
Figure 3:
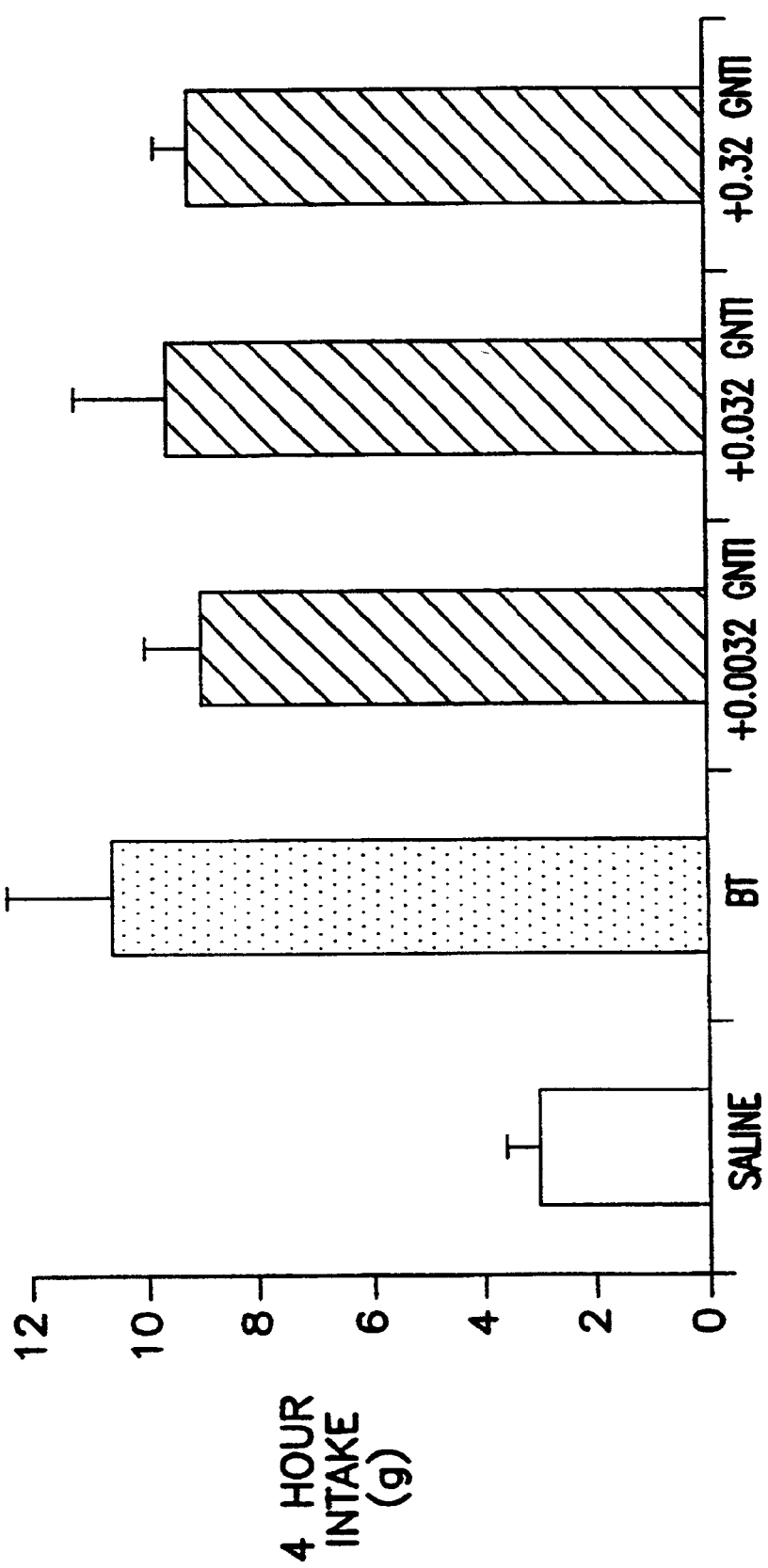
FIG. 3 Illustrates that GNTI does not decreases Butorphanol-induced feeding.
Figure 4:
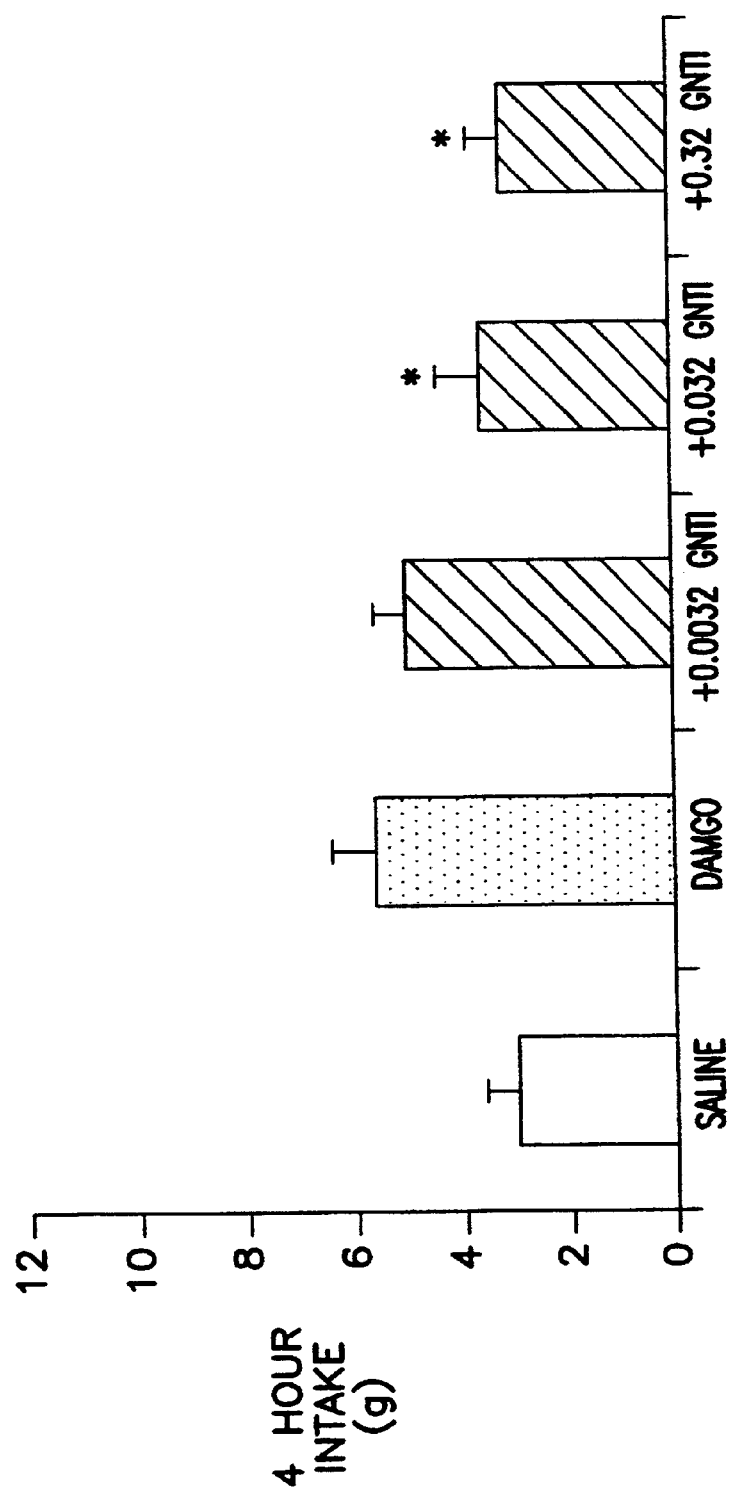
FIG. 4 Illustrates that GNTI decreases DAMGO-induced feeding.
Figure 5:
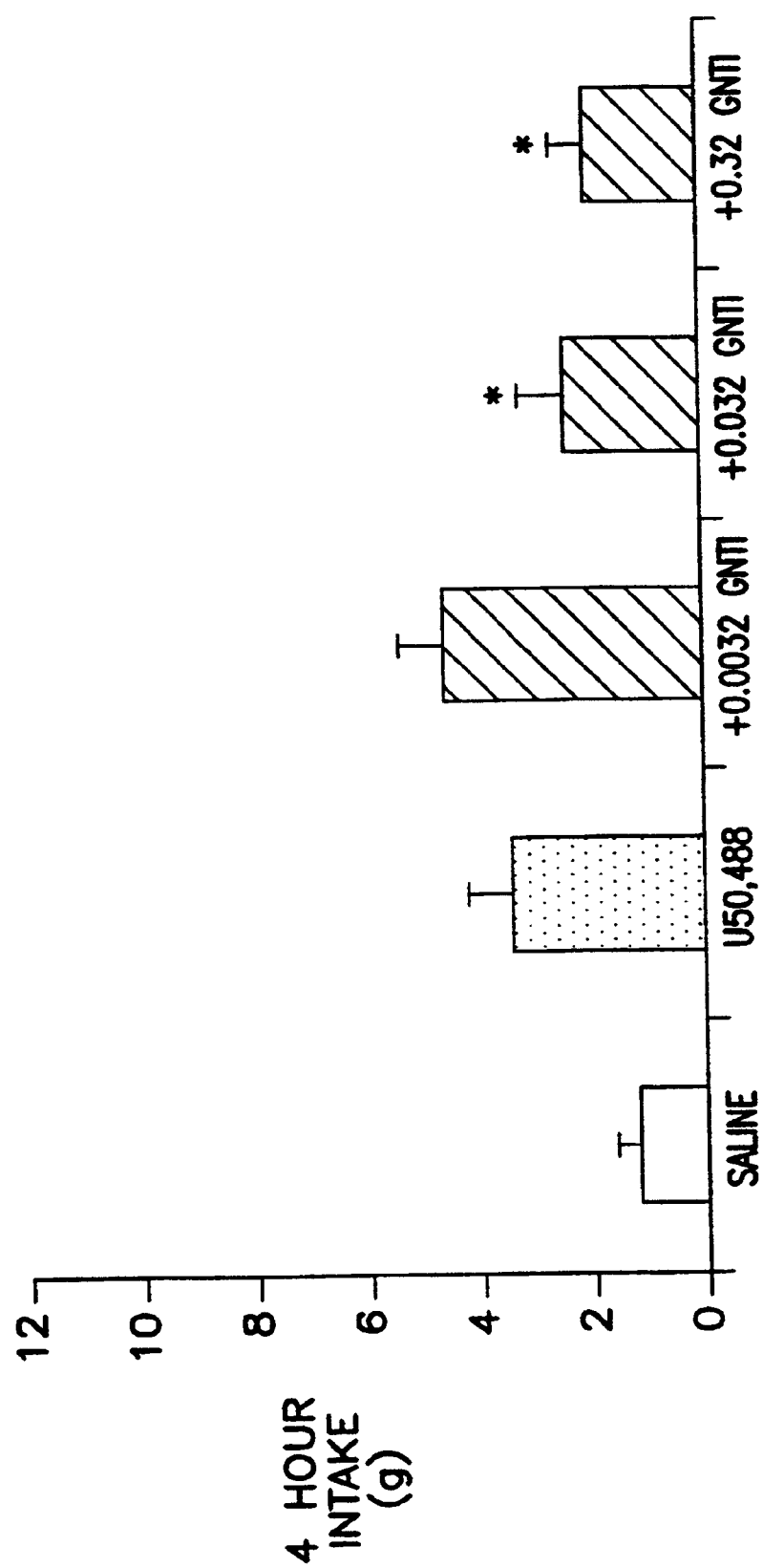
FIG. 5 Illustrates that GNTI decreases U50,488-induced feeding.
Figure 6:
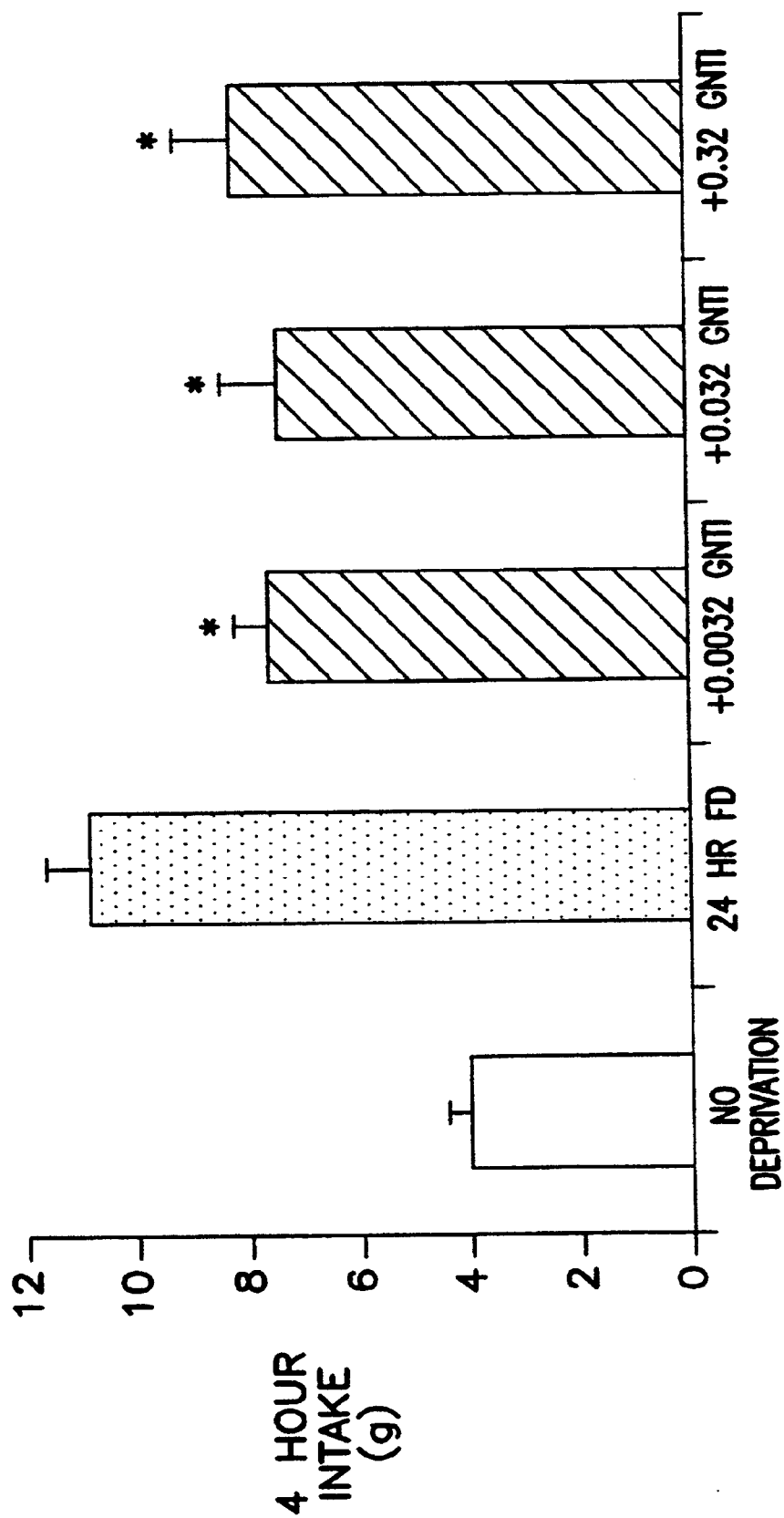
FIG. 6 Illustrates that GNTI decreases 24-hour deprivation-induced feeding.
Figure 7:
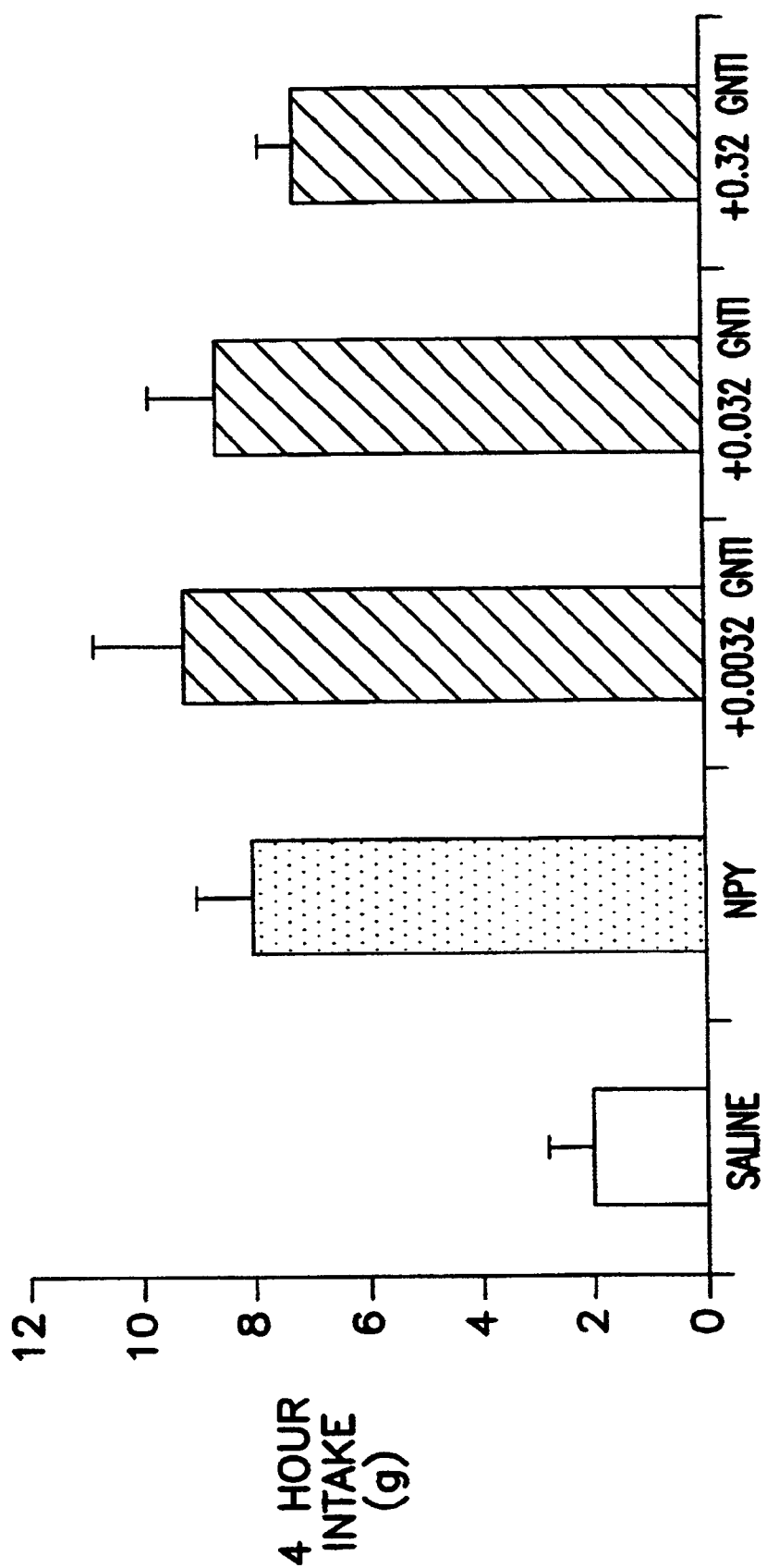
FIG. 7 Illustrates that GNTI does not decreases Neuropeptide Y-induced feeding.

Cyanoguanidines 10 maybe modified further as depicted in FIG. 2, scheme 6 to afford compounds of general formula 8 (see S. N. Thorn. *Tet.* vol 49, 31, 6885, 1993). Compounds of formula I wherein X is O or S can be prepared from intermediates structurally similar to 6 wherein NY has been replaced by O or S. These intermediates can be prepared as generally disclosed in U.S. Pat. No. 4,816,586, which is incorporated by reference herein, which also discloses methods suitable for the preparation of salts of compounds of general formula I.

4,5-Epoxy-6-ketomorphinans of general structure 3 (FIG. 1, scheme 1) can be prepared by synthetic methods which are well known in the art of organic chemistry (see U.S. Pat. No. 5,457,208 and citations therein).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to function as a kappa opioid receptor antagonist can be determined using pharmacological models which are well known to the art, or using one or more of the following assays.

Smooth Muscle Assays

1. Guinea Pig Ileal Longitudinal Muscle (GPI). Ilea from guinea pigs were taken approximately 10 cm from the ileocecal junction, and a strip of longitudinal muscle with the myenteric plexus attached was prepared by the method of H. B. Rang et al., *Brit. J Pharmacol.*, 1964, 22, 356. A 1 cm portion of this strip was then mounted between two platinum electrodes placed in a 10 ml organ bath and connected to an isometric transducer, contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 mM chloropheniramine maleate was the bathing solution and was continuously bubbled with 95% $O_2$ and 5% $CO_2$. The organ bath was maintained at 36–37° C. The longitudinal strip was allowed to equilibrate with continuous stimulation for a minimum of 90 min. Cumulative concentration-response curves were determined after drugs were added to the bath in preselected amounts and washed out with buffer after noting their maximum effects.

2. Mouse Vas Deferens (MvD). This assay was performed according to the description by G. Henderson et al., *Brit. J. Pharmacol.*, 1972, 46,764. Both vasa deferentia were dissected out of mice and mounted singly through two platinum electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in preselected amounts and washed out after noting their maximum effects.

Pharmacology

Each compound (100 nM or 20 nM where stated) was incubated for 15 min with the mouse vas deferens (MVD) and guinea pig ileum (GPI) preparations prior to adding graded doses of a standard agonist for determination of an $IC_{50}$ value. The standard agonists employed were [D-Ala$^2$, D-Leu$^5$]enkephalin (DADLE) (D), morphine (M) and ethylketazocine (EKC); these are selective for delta (D), mu (M) and kappa (EKC) opioid receptors, respectively. Concentration-response curves were obtained in the absence (control) and the presence of the antagonist and were determined as $IC_{50}$ values. The $IC_{50}$ ratio represents the $IC_{50}$ in the presence of the antagonist divided by the control IC$_{50}$ value in the same tissue. A concentration independent value of antagonist potency is calculated from the equation, K$_e$= [antagonist]/(IC$_{50}$ ratio-1). The results of these bioassays are summarized in Table 1.

Table 1

Summary of in Vitro Antagonist Potencies

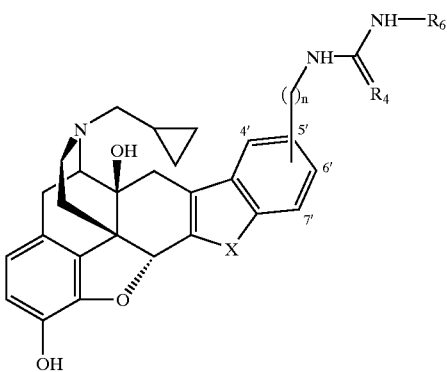

| | | | | Antagonist Potency K$_e$ (nM)$^b$ | | |
|---|---|---|---|---|---|---|
| | | | | κ(OP$_2$)$^a$ | μ_(OP$_3$)$^a$ | δ(OP$_1$)$^a$ |
| Entry | R$_4$ | Rpgd 6 | n | EKC | Morphine | DADLE |
| 15 | NH | H | 0 | 0.144* | 30.00 | 115 |
| 16 | NH | CH$_2$CH$_{33}$ | 0 | 0.157 | 19.00 | NT |
| 17 | NH | (CH$_2$)$_3$CH$_3$ | 0 | 0.09 | NT | NT |
| 18 | NH | H | 1 | 0.59 | 10.8 | NA |
| 19 | NCN | H | 0 | 3.13 | 16.13 | 9.08 |
| 20 | NCN | (CH$_2$)$_3$NMe$_2$ | 0 | 0.24 | 10.4 | NT |
| 21 | NCN | CH$_2$CH$_2$N⟨pyrrolidine⟩ | 0 | 0.47 | 5.71 | 126.6 |
| nor-Binaltorphimine (nor-BNI) | | | 2 | 0.56 | 13.7 | 10.6 |
| Naltrindole (NTI) | | | 1 | 45 | 29.4 | 0.13 |

$^a$GPI - determined using guinea pig ileum preparation.
$^b$K$_e$ = [antagonist]/(IC$_{50}$ Ratio − 1), where the IC$_{50}$ ratio is the IC$_{50}$ of the agonist in the presence of the antagonist divided by the IC$_{50}$ of the agonist alone in the same preparation. Antagonist concentration is 100 nM, * indicates 20 nM.
$^c$MVD - determined using mouse vas-deferens preparation. The agonists employed were ethylketazocine (EKC, κ-receptors), morphine (μ-receptors) and [D-Ala$^2$, D-Leu$^5$]enkephalin (DADLE, δ-receptors).
NT — not tested, NA — not active.

Summary of In Vivo Pharmacological Data Obtained for Compounds 15–21.

The compounds (15–21) showed potent antagonist activity towards the kappa opioid agonist ethylketazocine (EKC) in the GPI and they are considerably less effective at antagonizing the effect of morphine or DADLE. Thus, compounds 15–18 and 20–21 are all highly selective kappa opioid receptor antagonists. It is noteworthy that they are all more potent than the prototypical kappa antagonist nor-BNI and in this regard GNTI 15 exhibits selectivity ratios 9(κ/μ) and 42 (κ/δ) fold greater than that of nor-BNI. Compound (19) also demonstrated selectivity for the k opioid receptor.

In vivo studies (Table 2 and 3) indicate that compound (15) is a selective κ-antagonist. The fact that SC-administered compound (15) is greater than 50 times more potent than nor-BNI suggests that there is greater bioavailability.

TABLE 2

Antagonism of Selective Opioid Agonists, via ICV Administered Compound 15 (50 pmol) using the Mouse Tail Flick Assay.

| Agonist | ED$_{50}$ Ratio (limits) |
|---|---|
| U-50488H (κ) | 4.5 (3.4–6.3) |
| Morphine (μ) | 0.8 (0.5–1.2) |
| DSLET (δ) | 1.4 (1.0–2.2) |

DSLET : [D-Ser$^2$, D-Leu$^5$]-enkephalin-Thr$^6$ $^4$
(see : A. E. Takemori et al., J. Pharmacol. Exp. Ther., 190, 395–400, 1974)

TABLE 3

Antagonism of U-50488H Antiociception, by SC Administered Compound 15 and nor-BNI using the Mouse Abdominal Stretch Assay.

| Antagonist$^a$ | ED$_{50}$ Ratio (limits) |
|---|---|
| Compound (15) 2.0 μmol kg$^{-1}$ | 3.8 (2.5–6.3) |
| Compound (15) 0.05 μmol kg$^{-1}$ | 3.0 (1.9–5.0) |
| nor-BNI 2.5 μmol kg$^{-1}$ | 1.6 (1.2–2.3) |

$^a$U-50488H and the antagonists were administered SC.
(see : A. E. Takemori et al., Eur. J. Pharmacol., 16, 63, 1971)

Compound 15 (5'-guanidinyl-naltrindole; formula I wherein R$_1$=cyclopropylmethyl, R$_2$=OH, R$_3$=H, X =NH, R$_4$=NH, R$_5$ =NH, R$_6$=H ) or more specifically 5'-guanidinyl-17-cyclopropylmethyl-6,7-didehydro-4,5-α-epoxy-3,14-dihydroxyindolo[2',3':6,7]-morphinan ditrifluoroacetate dihydrate, displays potent and highly selective in vitro pharmacological kappa receptor antagonism. These data define clearly a dramatic change in the selectivity of NTI upon modification with a C5'-guanidinyl function. In addition, little, if any of the delta antagonist activity of NTI is associated with GNTI and that there is a concomitant increase in kappa antagonist potency (see F. M. Leslie, Pharmacol. Rev. 39, 3, 197, 1987). Antagonism of the selective kappa agonist U-50488H with GNTI indicates that it is 5-fold more potent and displays superior selectivity ratios for kappa over the mu and delta receptors when compared to the prototypical antagonist, nor-BNI.

Comparison of the Kappa Antagonist Potencies of Compound (15) and nor-BNI in the GPI$^2$

| | | | Selectivity Ratio$^c$ | |
|---|---|---|---|---|
| Antagonist | Agonist | K$_e$(pM)$^b$ | κ/μ | κ/δ |
| (15) | U-50488H | 41 | 728 | 2797 |
| nor-BNI | U-50488H | 200 | 69 | 53 |

$^a$GPI - guinea pig ileum preparation.
$^b$K$_e$ = [antagonist]/(IC$_{50}$ Ratio-1), where the IC$_{50}$ ratio is the IC$_{50}$ of the agonist in the presence of the antagonist divided by the IC$_{50}$ of the agonist alone in the same preparation.
$^c$The agonists employed were morphine (μ-receptors) and [D-Ala$^2$, D-Leu$^5$]enkephalin (δ-receptors).

The effects of mutational exchange of Glu297 in the κ receptor and Lys303 in the μ receptor on the binding affinity of representative compounds of the invention were examined using techniques known in the art. The results are reported in Table 4 below.

TABLE 4

Effect on Binding Affinity of Mutational Exchange of
Glu297 in the κ Receptor aud Lys303 in the μ Receptor

| compd | wt κ<br>$F_{ana}$[b] | κ[E297K]<br>$F_{mut}$[c] | wt μ<br>$F_{mut}$[c] | μ[K303E]<br>$F_{mut}$[c] |
|---|---|---|---|---|
| | $K_i \pm$ SEM (n), nM[a] | | | |
| nor-BNI | 0.12 ± 0.04 (8)<br>1.0 | 12.5 ± 0.92 (5)<br>123 | 101.9 ± 10.2 (3)<br>800 | 0.77 ± 0.13 (5)<br>9.3 |
| GNTI (15) | 0.09 ± 0.01 (3)<br>0.75 | 12.9 ± 0.48 (2)<br>143 | 9.23 ± 1.39 (3)<br>103 | 0.06 ± 0.02 (3)<br>0.67 |
| CNGNTI (19) | 0.27 ± 0.01 (3)<br>2.25 | 2.48 ± 0.82 (3)<br>9.2 | 4.04 ± 1.23 (3)<br>15 | 0.29 ± 0.05 (3)<br>1.1 |

[a]The $K_i$ values were determined in competition binding using [³H]diprenorphine in transiently expressed rat COS-7 cells and analyzed by whole cell binding. The number of individual determinations is indicated in parentheses (n).
[b]$F_{ana}$ = $K_i$(analog)/$K_i$(nor-BNI on the wt κ receptor).
[c]$F_{mut}$ = mutational factor, $K_i$(mutant receptor)/$K_i$(wt κ receptor).

The ability of a compound to decrease butorphanol-, DAMGO-, U50,488-, 24-hour deprivation-, and Neuropeptide Y-induced feeding can be determined using models known in the art. See for example, A. S. Levine et al., *Brain Research*, 1998, 534, 60–64; and D. C. Jewett, et al., 1998, *Society for Neuroscience Abstracts*, 1, Abstract #276.10, 705. Data for a representative compound of the invention is shown in FIGS. 3–7.

Kappa opioid receptor antagonists have potential therapeutic utility in pathologies where selective kappa opioid receptor blockade is desired such as suppression of appetite (see A. S. Levine, M. Grace, C. J. Billington, P. S. Portoghese. *Brain Research*. 534, 60, 1990), prevention of paralysis due to ischemic spinal trauma, as possible antipsychotic agents for treating possible endogenous dynorphin-A imbalances (see M. J. Millan. *TIPS*. 1990, 1, 70), and a variety of other physiological activities that may be mediated through kappa opioid receptors. As pharmacologic tools, these compounds can be used as probes for kappa opioid receptor structure and function.

The above data demonstrates that representative compounds of formula I are potent and selective kappa receptor antagonists. Accordingly, compounds of the invention are useful as therapeutic agents for the treatment of diseases or conditions wherein kappa receptor activity is implicated and antagonism of kappa receptors is indicated. Additionally, compounds of the invention are useful as pharmacological tools for the further investigation of kappa receptor pharmacology.

The invention will now be illustrated by the following non-limiting Examples. All reagents were obtained from the Aldrich Chemical Company unless stated otherwise. Naltrexone free base was obtained from Mallinkrodt. All reactions described were conducted in an inert atmosphere of argon or nitrogen unless otherwise stated. Flash column chromatography was performed using silica gel (200–400 mesh, BET surface area 500 m²/g, pore volume 0.75 cm³/g Aldrich Chemical Company) as the stationary phase and nitrogen. Thin layer chromatography was performed using silica gel 60 $F_{254}$ aluminium backed sheets (E. Merck). Chromatographic elution solvent systems are reported as volume: volume ratios. Infra-red (I.R) spectra were recorded on a Perkin-Elmer PE-281 spectrophotometer or a Nicolet 5DXC FT-IR spectrometer as potassium bromide (KBr) discs. NMR spectra were obtained using the Glide software package operating on a Sun Sparc Station 5 with Varian Unity 300 MHZ or Varian Inova 300 MHZ instruments at room temperature using $CD_3OD$, $CDCl_3$ or $(CD_3)_2S=O$ as solvents. The δ-scale (ppm) was in reference to the deuterated solvent. Coupling constants (J) are reported in hertz (Hz). Low resolution (LRFABMS) and high resolution (HRFABMS) mass spectra were obtained on a VG-707EHF spectrometer using a m-nitro benzyl alcohol (MNOBA) matrix. Melting points were determined on a Thomas-Hoover melting point apparatus and stand uncorrected. RPHPLC was carried out using a Beckman Isocratic Liquid Chromatograph Model 330 employing a Dynamax macro HPLC column (Rainin Instrument Co., Woburn, Mass.) Compounds were detected using a Beckman Optical Unit and Hewlett Packard 3390A Integrator. Elemental combustion analyses were carried out by MHW Laboratories, Phoenix, Ariz. or by Galbraith Laboratories, Knoxville, Tenn.

EXAMPLE 1

5'-Guanidinyl-17-cyclopropylmethyl-6,7-didehydro-4,5-α-epoxy-3.14-dihydroxyindolo[2',3':6,7] morphinan Ditrifluoroacetate Dihydrate (15)

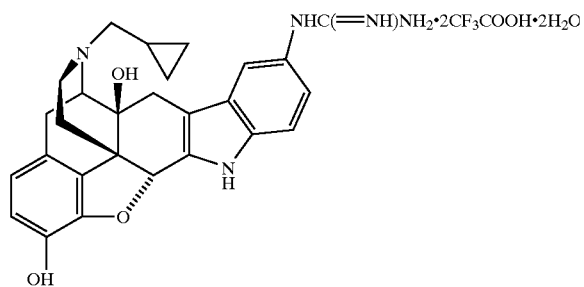

Compound (22) (200 mg, 0.29 mmol) was dissolved in anhydrous dichloromethane (250 ml) under a stream of nitrogen and cooled to 0° C. This solution was stirred rapidly for 15 minutes and then TFA (10 eqv., 230 μl) was added dropwise over a 10 minute period. Rapid stirring was maintained for a further 48 hours at ambient temperature. The volatile components were removed under reduced pressure and the resultant oil was washed with diethyl ether. This produced a white precipitate that was isolated by vacuum filtration. The crude solid product was dissolved in water and purified by RP-HPLC to afford the title compound as a clear glass. Yield: 177 mg, 0.24 mmol, 82.3%, mpt.:

178–185° C. (decomp.). Reverse Phase HPLC Conditions: Elution: 90% Water, 10% MeCN, 0.25% TFA. Flow rate 3.0 ml/min. Retention time 5.86 min. $^1$H NMR 300 MHZ CD$_3$OD δ (ppm): 7.44 (d, 1H, H7', $^3$J$_{7'-6'}$=8.51 Hz); 7.34 (d, 1H, H', $^4$J$_{4'-6'}$=2.01 Hz); 7.00 (dd, 1H, H6', $^3$J$_{6'-7'}$=8.60 Hz, $^4$J$_{6'-4'}$=2.01 Hz); 6.67 (d, 1H, H2, $^3$J$_{2-1}$=8.24 Hz); 6.64 (d, 1H, H1, $^3$J$_{1-2}$=8.15 Hz); 5.72 (s, 1H, H5); 4.21 (d, 1H, J=6.04 Hz); 3.42–3.29 (m, 3H); 3.20–3.15 (m, 1H); 3.03–2.86 (m, 3H); 2.80–2.68 (m, 2H); 1.95–1.91 (m, 1H); 1.29–1.11 (m, 1H); 0.90–0.74 (m, 2H); 0.59–0.50 (m, 2H). $^{13}$C NMR 75.48 MHZ CD$_3$OD δ (ppm): 158.04 (NH C(=NH)NH$_3^+$ guanidine); 144.06; 141.37; 137.45; 131.75; 129.54; 127.76; 126.19; 121.88; 121.44; 119.87; 118.60; 117.26; 113.37; 109.33; 105.01; 84.12; 72.83; 62.86; 58.13; 46.78; 29.42; 28.98; 28.95; 24.22; 6.09; 5.45; 2.58. I.R. KBr disc ν (cm$^{-1}$): 3386.1 (bs); 2963.17 (w); 1677.69 (s, guanidine); 1505.16 (m); 1462.69 (m); 1430.24 (w); 1326.92 (m); 1202.09 (s); 1132.32 (s); 1060.26 (w); 1029.05 (w); 869.14 (w); 836.20 (m); 800.61 (m); 721.26 (m). LR-FABMS MNOBA matrix m/z (%): 473.2 (M+2$^+$, 25); 472.2 (C$_{27}$H$_{29}$N$_5$O$_3$+H$^+$, 100, base peak & parent ion); 471.2 (M+, 25). HR-FABMS MNOBA matrix for C$_{27}$H$_{29}$N$_5$O$_3$+H$^+$: calculated: 472.5687, observed: 472.2326. CHN analysis for C$_{27}$H$_{29}$N$_5$O$_3$.2TFA.2H$_2$O: Calculated: C (50.61); H (4.78); N (9.52). Found: C (50.42); H (4.77); N (9.06).

The intermediate compound (22) was prepared as follows.

a. 5'-Nitro-17-(cyclopropylmethyl)-6,7-didehydro-4,5α-epoxy-3,14-dihydroxyindolo[2',3':6,7]morphinian (5a)

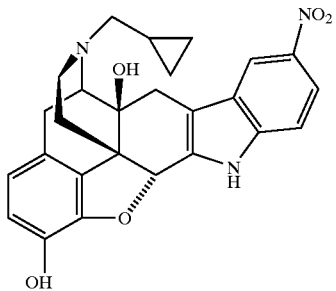

Naltrexone hydrochloride (3) (R$_1$=CPM, R$_3$=H, R$_2$=OH) (15.0 g, 39.7 mmol) and 4-nitrophenylhydrazine (4) (6.80 g, 44.4 mmol, 1.1 equiv.) in glacial acetic acid (90 ml) was heated at 100° C. for 1 hour. Concentrated HCl (90 ml) was added and the mixture was stirred at 100–110° C. for 7 days. The cooled reaction mixture was, diluted with water (200 ml), and neutralized with solid NaHCO$_3$. The suspension was extracted with ethyl acetate (5×100 ml) dried (Na$_2$SO$_4$), and concentrated in vacuo. The residual oil was purified by silica gel flash chromatography [94.5:5:0.5 dichloromethane-methanol-NH$_4$OH]. Product was recovered as an amorphous yellow foam Yield: 11.67 g, 65%, 25 mmol. $^1$H NMR 300 MHZ d$_6$-DMSO δ (ppm): 12.31 (s, 1H), 9.5 (bs, 1H), 9.1 (bs, 1H), 8.25 (s, 1H, H4'), 7.84 (d, $^3$J=9 HZ, 1H, H6'), 7.45 (d, $^3$J$_{7'-6'}$=9 Hz, 1H, H7'), 6.74 (d, 1H, H2, $^3$J$_{2-1}$=8 Hz,), 6.58 (d, 1H, H1, $^3$J$_{1-2}$=8 Hz), 5.70 (s, 1H), 4.20 (d, J=5 Hz, 1H), 3.8 (br s, 1H), 3.42(d, J=19 Hz, 1H), 2.9–3.3 (m, 5H), 2.63 (m, 2H), 2.52 (m, 1H), 1.73 (d, J=7 Hz, 1H), 1.09 (m, 1H), 0.66 (m, 1H), 0.58 (m, 1H), 0.48 (m, 1H), 0.39 (m, 1H); $^{13}$C NMR 75.48 MHZ d$_6$-DMSO δ (ppm): 144.07, 141.87, 141.28, 141.14, 134.61, 129.96, 126.55, 122.50, 121.26, 120.38, 119.11, 118.47, 116.71, 113.05, 112.35, 83.47, 73.11, 63.14, 61.91, 57.90, 47.26, 29.67, 29.08, 26.57, 6.89, 6.33, 0.77; HRFABMS MNOBA matrix for C$_{26}$H$_{28}$N$_3$O$_3$+H$^+$: Calculated: 460.1872 [M+H]$^+$, observed: 460.1868.

b. 5'-Amino-17-(cyclopropylmethyl)-6,7-didehydro-4,5α-epoxy-3,14-dihydroxyindolo[2',3':6,7]morphinian (6) (n=0):

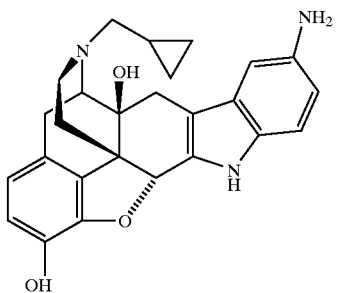

To a rapidly stirring solution (5a) (7.4 g 16.1 mmol) in methanol (200 ml) was added Raney Nickel (approx. 2.50 g). Hydrazine monohydrate (6 ml, 124 mmol, 7.7 eq) was added dropwise. The reaction was stirred under nitrogen for 24 hours. At this stage evolution of nitrogen and hydrogen had ceased and the colorless solution was subsequently filtered under vacuum through a Celite 512 plug. The filtrate was concentrated in vacuo and purified by silica gel flash chromatography [94.5:5:0.5, dichloromethane-methanol-NH$_4$OH]. The title compound was isolated as a white powder. Yield: 4.74 g, 15.6 mmol, 70%. $^1$H NMR 300 MHZ d$_6$-DMSO δ (ppm): 10.59 (s, 1H, OH), 8.93 (bs, 1H, N Hindole), 7.01 (d, 1H, H7', $^3$J=9 Hz), 6.44–6.56 (m, ArH, 4H), 5.43 (s, 1H, H5β), 4.72 (bs, 1H), 4.42 (bs, 1H), 3.45 (d, 1H), 3.03 (d, 1H), 2.6–2.8 (m, 2H), 2.54 (d, J=15 Hz, 1H), 2.3–2.5 (m, 4H), 2.1–2.3 (m, 2H), 1.55 (d, J=11.5 Hz, 1H), 0.86 (m, 1H), 0.48 (m, 2H), 0.12 (m, 2H). $^{13}$C NMR 75.48 MHZ d$_6$-DMSO δ (ppm): 144.25, 141.86, 140.89, 132.23, 131.75, 130.55, 128.16, 125.36, 119.22, 117.93, 113.84, 112.58, 109.66, 102.66, 85.39, 73.29,62.99, 59.79, 48.33, 44.39, 32.29, 29.94, 10.35, 4.88, 4.75. HRFABMS MNOBA matrix for C$_{26}$H$_{27}$N$_3$O$_3$+H$^+$ observed: 430.2127 [M+H]$^+$. Calculated: 430.2131.

c. 5-[N,N'-Bis-tert-butoxycarbonyl]guanidinyl-17-cyclopropylmethyl-6,7-didehydro4,5-α-epoxy-3,14-dihydroxyindolo[2',3':6,7]morphinan (22)

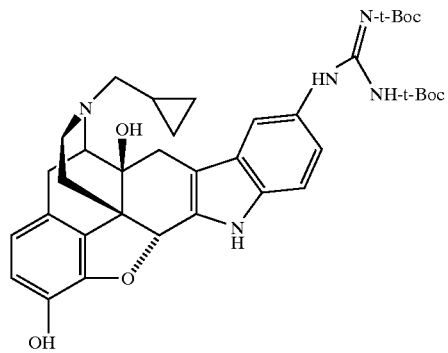

5'-Aminonaltrindole (6) (n=0) (646 mg, 1.5 mmol) was dissolved in anhydrous DMF (3.0 ml) in a previously flame dried 5 ml round bottom flask that had been purged with N$_2$ (g) and cooled to 0° C. on an ice bath. Bis-Boc-thiourea (8) (R$_6$=H) (1.1 eqv., 1.654 mmol, 275 mg), triethylamine (2.2 eqv., 461.3 μl) were added sequentially and the reaction mixture stirred for 10 minutes at 0° C. Mercury (II) chloride (1.1 eqv., 449 mg) was added in one portion and rapid stirring was maintained for 20 minutes, after which the ice bath was removed and the reaction mixture allowed to attain room temperature for 1 hour. The mixture was filtered through a celite clay pad under vacuum to remove mercuric sulphide and the cake was subsequently washed repeatedly with methanol. Removal of all volatile components under reduced pressure produced a brown oil which was subjected to flash column chromatography [elution system 80:10:1, $CHCl_3$, MeOH, $NH_3$] to afford the title compound as a white crystalline solid. Yield: 781 mg, 1.14 mmol, 76%. $^1H$ NMR 300 MHZ $CDCl_3$ δ (ppm): 10.14 (bs, 1H); 9.42 (bs, 1H); 7.35 (d, 1H, H4', $^3J$=1.74 Hz); 7.18 (d, 1H, ArH); 7.08 (d, 1H, ArH, $^3J$=8.70 Hz); 6.54 (d, 1H, H2, $^3J$=8.15 Hz); 6.47 (d, 1H, H1, $^3J$=8.15 Hz); 5.56 (s, 1H, H5); 3.38–2.38 (m, 9H); 1.72 (m, 1H); 1.45 (s, 9H, 'Bu); 1.38 (s, 9H, 'Bu); 0.93–0.89 (m, 1H); 0.54–0.52 (m, 2H); 0.14–0.12 (m, 2H). $^{13}C$ NMR $CDCl_3$ 75.48 MHZ δ (ppm): 163.68; 154.41; 153.36; 143.16; 139.51; 139.48; 135.41; 135.34; 131.46; 130.67; 130.30; 127.97; 126.61; 124.60; 119.37; 118.79; 117.32; 117.21; 113.81; 111.44; 110.98; 109.99; 84.96; 83.45; 79.45; 72.80; 62.38; 59.46; 50.36; 49.73; 47.88; 43.60; 31.35; 28.69; 28.08; 23.12; 9.33; 3.91; 3.84. HR-FABMS MNOBA matrix for $C_{37}H_{45}N_5O_7$: Calculated $[M+H]^+$ 672.8085, observed $[M+H]^+$ 672.3387.

EXAMPLE 2

5'-N-Ethylguanidinyl-17-cyclopropylmethyl-6,7-didehydro-4,5-α-epoxy-3,14-dihydroxyindolo[2',3':6,7]morphinan Ditrifluoroacetate Dihydrate (16)

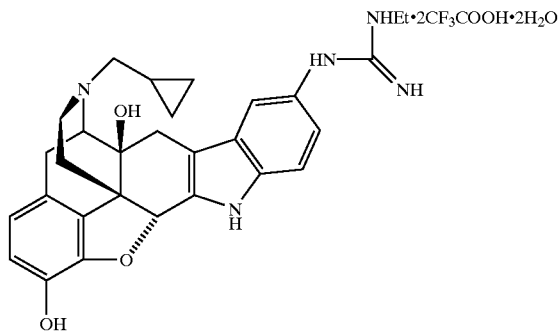

5'-[N-Ethyl,N'-tert-butoxycarbonyl]guanidinyl-17-cyclopropylmethyl-6,7-didehydro-4,5-α-epoxy-3,14-dihydroxyindolo[2',3':6,7]morphinan (200 mg, 0.33 mmol) was dissolved in anhydrous dichloromethane (8 ml) under a stream of nitrogen and cooled to 0° C. This solution was stirred rapidly for 15 minutes and then TFA (2 ml) was added dropwise over a 10 minute period. Rapid stirring was maintained for a further 48 hours at ambient temperature. The volatile components were removed under reduced pressure and the resultant oil was washed with diethyl ether. This produced a white precipitate that was isolated by vacuum filtration. The crude solid product was dissolved in water and purified by RP-HPLC to afford the title compound as a clear glass. Yield: 173 mg, 0.23 mmol, 93%, mpt.: 176–178° C. (decomp.). $^1H$ NMR 300 MHZ $CD_3OD$ δ (ppm): 7.50 (d, 1H, H7', $^3J_{7'-6'}$=8.60 Hz); 7.33 (d, 1H, H4', $^4J_{4'-6'}$=183 Hz); 7.01 (dd, 1H, H6', $^3J_{6'-7'}$=8.6 Hz, $^4J_{6'-4'}$=2.01 Hz); 6.60 (m, 2H, H1 & H2, Ar$\underline{H}$); 5.73 (s, 1H, H5β); 4.23 (d, 1H, J=6.00 Hz); 3.49–3.16 (m, 6H); 3.03–2.80 (m, 3H); 2.79–2.68 (m, 2H); 1.96–1.92 (m, 1H); 1.40–1.16 (m, 4H, including embedded t, 3H, $CH_2C\underline{H}_3$, J=7.23 Hz); 0.94–0.74 (m, 4H); 0.54 (m, 2H). $^{13}C$ NMR 75.48 MHZ $CD_3OD$ δ (ppm): 158.98 (NH$\underline{C}$(=NH)NEtH$_2^+$ guanidine); 156.01; 143.37; 140.69; 136.72; 131.05; 128.89; 127.12; 125.62; 121.26; 120.99; 119.29; 116.77; 112.43; 108.69; 83.49; 72.19; 62.18; 59.68; 57.48; 36.15; 28.78; 27.83; 23.60; 10.07; 5.42; 4.85; 1.96. I.R. KBr disc ν (cm$^{-1}$): 3198.31 (bs); 1677.28 (s, guanidine); 1505.29 (m); 1462.57 (m); 1430.68 (w); 1386.49 (m); 1242.52; 1201.59 (s); 1132.76 (s); 1061.06 (w); 1029.24 (w); 913.85 (w); 868.40 (w); 835.36 (m); 800.05 (m); 721.16 (m). LR-FABMS MNOBA matrix m/z (%): 500.3 (M+H$^+$, 100); 499.3 ($C_{29}H_{33}N_5O_3^+$, 26, base peak & parent ion). HR-FABMS MNOBA matrix for $C_{29}H_{33}N_5O_3$+H$^+$: calculated: 500.6227, observed: 500.2647. CHN analysis for $C_{29}H_{33}N_5O_3$·2TFA·2H$_2$O: Calculated: C (51.90); H (5.15); N (9.17). Found: C (51.62); H (5.07); N (9.02).

The intermediate 5'-[N-ethyl,N'-tert-butoxycarbonyl] guanidinyl-17-cyclopropylmethyl-6,7-didehydro-4,5-α-epoxy-3,14-dihydroxyindolo[2',3':6,7]morphinan was prepared as follows.

a. 5'-[N-Ethyl,N'-tert-butoxycarbonyl]guanidinyl-17-cyclopropylmethyl-6,7-didehydro-4,5-α-epoxy-3,14-dihydroxyindolo[2',3':6,7]morphinan 5'-Aminonaltrindole (6) (n=0) (100 mg, 0.23 mmol) was dissolved in anhydrous DMF (3.0 ml) in a previously flame dried 5 ml round bottom flask that had been purged with N$_2$ (g) and cooled to 0° C. on an ice bath. N-Ethyl-N'-BOC-thiourea (8) (R$_6$=Et) (1 eqv., 0.233 mmol, 44.3 mg), triethylaminie (2.2 eqv., 71 μt) were added sequentially and the reaction mixture stirred for 10 minutes at 0° C. Mercury (II) chloride (1 eqv., 63.2 mg) was added in one portion and rapid stirring was maintained for 20 minutes, after which the ice bath was removed and the reaction mixture allowed to attain room temperature for 1 hour. The mixture was filtered through a celite clay pad under vacuum to remove mercuric sulphide and the cake was subsequently washed repeatedly with methanol. Removal of all volatile components under reduced pressure produced a brown oil which was subjected to flash column chromatography [elution system 80:10:1, $CHCl_3$, MeOH, $NH_3$] to afford the title compound as a white crystalline solid. Yield: 89 mg; 65.4%.

5'-Aminonaltrindole (6) (n=0) can be prepared by the methods as described herein above in Example 1.

EXAMPLE 3

5'-N-Butylguanidinyl-17-cyclopropylmethyl-6,7-didehydro4,5α-epoxy-3,14-dihydroxyindolo[2',3':6, 7]morphinan Ditrifluoroacetate Dihydrate (17)

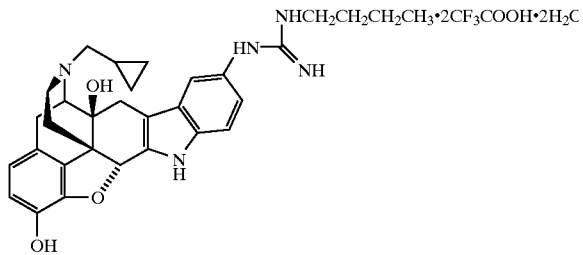

5'-[N-Butyl,N'-tert-butoxycarbonyl]guanidinyl-17-cyclopropylmethyl-6,7-didehydro4,5-α-epoxy-3,14-dihydroxyindolo[2',3':6,7]morphinan (100 mg, 0.16 mmol) was dissolved in anhydrous dichloromethane (10 ml) under a stream of nitrogen and cooled to 0° C. This solution was stirred rapidly for 15 minutes and then TFA (3 ml) was added dropwise over a 10 minute period. Rapid stirring was maintained for a further 48 hours at ambient temperature. The volatile components were removed under reduced pressure and the resultant oil was washed with diethyl ether. This produced a white precipitate that was isolated by vacuum filtration. The crude solid product was dissolved in water and purified by RP-HPLC to afford the title compound as a clear glass. Yield: 105 mg, 0.133 mmol, 83%, mpt.: 188–191° C. (decomp.). $^1$H NMR 300 MHZ CD$_3$OD δ (ppm): 7.45 (d, 1H, H7', $^3J_{7'-6'}$=8.60 Hz); 7.33 (d, 1H, H4', $^4_4J_{4'-6'}$=1.92 Hz); 7.01 (dd, 1H, H6', $^3J_{6'-7'}$=8.6 Hz, $^4J_{6'-4'}$=1.92 Hz); 6.66 (m, 2H, H1 & H2, ArH); 5.73 (s, 1H, H5β); 4.23 (d, 1H, J=6.13 Hz); 3.50–3.17 (m, 6H); 3.03–2.94 (m, 3H); 2.77–2.68 (m, 2H); 1.95 (m, 1H); 1.58 (m, 2H, CH$_2$CH$_2$, $^3$J=7.23 Hz); 1.40 (m, 2H, CH$_2$CH$_2$, $^3$J=7.7 Hz); 1.34 (m, 2H, J=7.26 Hz); 0.96 (t, 3H, CH$_2$CH$_3$, J7.32 Hz); 0.91–0.75 (2 sets of multiplets, 3H, CPM); 0.54 (m, 2H). I.R. KBr disc ν (cm$^{-1}$): 3198.31 (bs); 1677.28 (s, guanidine); 1505.29 (m); 1462.57 (m); 1430.68 (w); 1386.49 (m); 1242.52; 1201.59(s); 1132.76 (s); 1061.06 (w); 1029.24 (w); 913.85 (w); 868.40(w); 835.36 (m); 800.05 (m); 721.16 (m). LR-FABMS MNOBA matrix m/z (%): 528.4 (M+H$^+$, 100); 527.4 (C$_{31}$H$_{37}$N$_5$O$_3^+$, 31, base peak & parent ion). HR-FABMS MNOBA matrix for C$_{31}$H$_{37}$N$_5$O$_3$+H$^+$: calculated: 527.2896, observed: 527.2985. CHN analysis for C$_{31}$H$_{37}$N$_5$O$_3$.2TFA.2H$_2$O: Calculated: C (53.10); H (5.48); N (8.85). Found: C (52.91); H (5.13); N (8.47).

The intermediate 5'-[N-Butyl,N'-tert-butoxycarbonyl]guanidinyl-17-cyclopropylmethyl-6,7-didehydro-4,5-α-epoxy-3,14-dihydroxyindolo[2',3':6,7]morphinan was prepared as follows.

a. 5'-[N-Butyl,N'-tert-butoxycarbonyl]guanidinyl-17-cyclopropylmethyl-6,7-didehydro4,5-α-epoxy-3,14-dihydroxyindolo[2',3':6,7]morphinan 5'-Aminonaltrindole (6) (n=0) (121.2 mg, 0.28 9mol) was dissolved in anhydrous DMF (3.0 ml) in a previously flame dried 5 ml round bottom flask that had been purged with N$_2$ (g) and cooled to 0° C. on an ice bath. N-Butyl-N'-BOC-thiourea (8) (R$_6$=Bu) (1 eqv., 0.28 mmol, 66 mg), triethylamine (2.2 eqv., 71 μt) were added sequentially and the reaction mixture stirred for 10 minutes at 0° C. Mercury (II) chloride (eqv., 77 mg) was added in one portion and rapid stirring was maintained for 20 minutes, after which the ice bath was removed and the reaction mixture allowed to attain room temperature for 1 hour. The mixture was filtered through a celite clay pad under vacuum to remove mercuric sulphide and the cake was subsequently washed repeatedly with methanol. Removal of all volatile components under reduced pressure produced a brown oil which was subjected to flash column chromatography [elution system 80:10:1, CHCl$_3$, MeOH, NH$_3$] to afford the title compound as a white crystalline solid. Yield: 121 mg; 0.193 mmol, 68%.

5'-Aminonaltrindole (6) (n=0) can be prepared by the methods as described herein above in Example 1.

EXAMPLE 4

5'-Methylguanidinyl-17-cyclopropylmethyl-6,7-didehydro4,5α-epoxy-3,14-dihydroxyindolo[2',3':6,7]morphinan Ditrifluoroacetate Dihydrate (18)

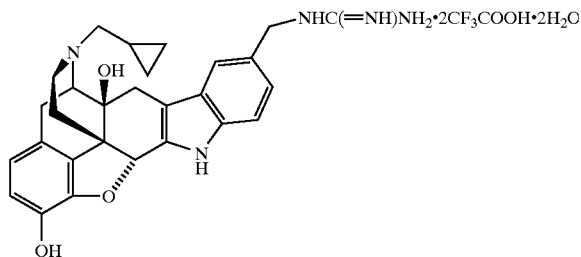

Compound 23 (150 mg, 0.22 mmol) was dissolved in anhydrous dichloromethane (10 ml) under a stream of nitrogen and cooled to 0° C. This solution was stirred rapidly for 15 minutes and then TFA (2 ml) was added dropwise over a 10 minute period. Rapid stirring was maintained for a further 48 hours at ambient temperature. The volatile components were removed under reduced pressure and the resultant oil was washed with diethyl ether. This produced a white precipitate that was isolated by vacuum filtration to afford the title compound as an off white solid. Yield: 151 mg, 0.2 mmol, 91%. $^1$H NMR 300 MHZ CD$_3$OD δ (ppm): 7.38 (m, 2H, ArH, H4'&H7'); 7.11 (dd, 1H, H6', $^3J_{6'-7'}$=8.60 Hz, $^4J_{6'-4'}$=1.46 Hz); 6.67 (m, 2H, ArH, H1&H2); 5.72 (s, 1H, H5); 4.41 (s, 2H, CH$_2$NHC(=NH)NH$_2$); 4.21 (d, 1H, J=6.04 Hz); 3.42–3.29 (m, 3H); 3.20–3.15 (m, 1H); 3.03–2.86 (m, 3H); 2.80–2.68 (m, 2H); 1.95–1.91 (m, 1); 1.29–1.11 (m, 1H); 0.90–0.74 (m, 2H); 0.59–0.50 (m, 2H). IR KBr disc ν (cm$^{-1}$): 3374.05; 1679.11; 1504.93; 1462.58; 1431.85; 1328.01; 1202.20; 1135.29; 1060.20; 1029.46; 1011.47; 929.80; 911.89; 868.08; 837.96; 800.38; 721.89; 597.48. HR-FABMS MNOBA matrix for C$_{28}$H$_{31}$N$_5$O$_3$+H$^+$: calculated: 486.5885, observed: 486.2507. CHN analysis for C$_{28}$H$_{31}$N$_5$O$_3$.2TFA.2H$_2$O: Calculated: C (51.34); H (4.85); N (9.36). Found: C (51.12); H (4.64); N (9.17).

a. 5'-Aminomethyl-17-(cyclopropylmethyl)-6,7-didehydro-4,5α-epoxy-3,14-dihydroxyindolo[2',3':6,7]morphinian (6) (n=1)

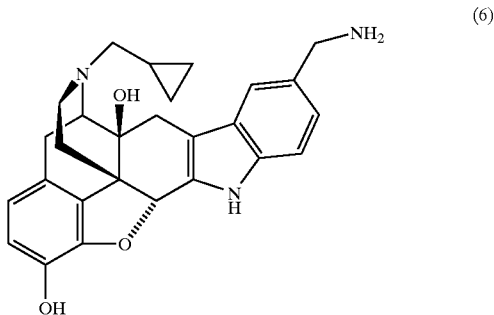

To a solution of nitrile (5b) (2.00 g, 1.27 mmol) in absolute ethanol (27 ml) and NH$_4$OH (3 ml) was added Raney Nickel (500 mg). The suspension was hydrogenated at a pressure of 70–75 psi for 3 days and then additional Raney nickel (ca. 300 mg) was added. Hydrogenation was continued for another 2 days then the reaction was quickly filtered and concentrated in vacuo. The residue was purified by silica gel flash column chromatography (78:20:2 dichloromethane-methanol-NH$_4$OH) affording the product as a slightly pink powder, yield: 1.09 g (63%); silica gel TLC R$_f$0.37 (78:20:2 dichloromethane-methanol-NH$_4$OH). $^1$H NMR 300 MHZ (d$^6$-DMSO) δ (ppm): 11.02 (s, 1H, —OH), 7.25 (s, 1H, H$_{4'}$), 7.21 (d, J=8.5 Hz, H$_{7'}$), 7.02 (d, J=8.5 Hz, 1H, H$_{6'}$), 7.49 (d, J=8 Hz, 1H, H$_2$), 7.44 (d, J=8 Hz, 1H, H$_1$), 5.47 (s, 1H, H$_5$), 4–5 (3 br s, —NH$_2$, —OH), 3.70 (s, 2H, —CH$_2$NH$_2$), 3.23 (d, J=6 Hz, 1H), 3.02 (d, J=9 Hz, 1H), 2.6–2.8 (m, 3H), 2.2–2.5 (m, 4H), 2.11 (dt, J=3, 12 Hz, 1H), 1.55 (br d, J=11.5 Hz, 1H), 0.86 (m, 1H, H$_{18}$), 0.47 (m, 2H, H$_{20}$, H$_{20'}$), 0.11 (m, 2H, H$_{19}$, H$_{19'}$); $^{13}$C NMR (DMSO-d$_6$) δ 140.99, 136.86, 134.90, 132.11, 130.99, 127.25, 125.28, 123.04, 119.29, 117.95, 117.69, 112.06, 110.95, 85.10, 73.27, 62.92, 59.76, 48.42, 47.18, 44.34, 32.23, 29.88, 23.81, 10.36, 4.85, 4.68.

b. 5'-Methyl-bis-Boc-guanidinyl-17-cyclopropylmethyl-6,7-didehydro-4,5-α-epoxy-3,14-dihydroxyindolo[2',3':6,7]morphinan (23)

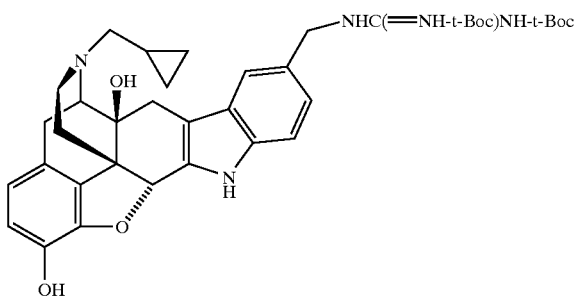

5'-Methylaminonaltrindole (6) (n=1) (200 mg, 0.451 mmol) was dissolved in anhydrous DMF (4.0 ml) in a previously flame dried 5 ml round bottom flask that had been purged with N$_2$ (g) and cooled to 0° C. on an ice bath. Bis-Boc-thiourea (8) (R$_6$=H) (1.1 eqv., 0.496 mmol, 137 mg), triethylamine (2.2 eqv., 138 μl) were added sequentially and the reaction mixture stirred for 10 minutes at 0° C. Mercury (II) chloride (1.1 eqv., 135 mg) was added in one portion and rapid stirring was maintained for 20 minutes, after which the ice bath was removed and the reaction mixture allowed to attain room temperature for 1 hour. The mixture was filtered through a celite clay pad under vacuum to remove mercuric sulphide and the cake was subsequently washed repeatedly with methanol. Removal of all volatile components under reduced pressure produced a brown oil which was subjected to flash column chromatography [elution system 80:1, CHCl$_3$, MeOH] to afford the title compound as a white crystalline solid. Yield: 229 mg, 0.34 mmol, 69%. $^1$H NMR 300 MHZ CD$_3$OD δ (ppm): 7.51 (s, 1H, H4'); 7.40 (d, 1H, H7', $^3$J=8.34 Hz); 7.18 (dd, 1H, H6', $^3$J=8.42 Hz, $^4$J=1.41 Hz); 6.64 (s, 2H, H1&H2, ArH); 5.68 (s, 1H, H5β); 4.12 (s, 2H, CH$_2$); 4.03 (bs, 1H); 3.38–2.38 (m, 9H); 1.72 (m, 1H); 1.45 (s, 9H, $^t$Bu); 1.38 (s, 9H, $^t$Bu); 0.93–0.89 (m, 1H); 0.54–0.52 (m, 2H); 0.14–0.12 (m, 2H).

EXAMPLE 5

5'-N'-Cyano-N-[17-(cyclopropylmethyl)-6,7-didehydro4.5α-epoxy-3,14-dihydroxyindolo[2',3':6,7]morphinian]-Guanidine (19)

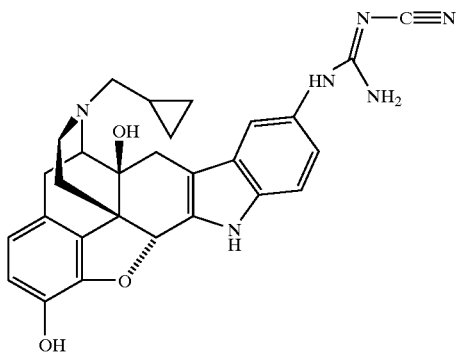

O-Phenylisourea (24) (100 mg, 0.18 mmol) was dissolved in a 30% NH$_4$OH:EtOH solution 10 ml. The reaction bottle was sealed with a screw cap containing a teflon liner and the contents were stirred vigorously at 60° C. for 24 hours. Volatile components from the cooled reaction mixture were removed in vacuo and the title compound was isolated following flash chromatographic purification [EtOAc:MeOH:NH$_3$, 98:1:1] as an off white amorphous foam. Yield: 0.134 mmol, 66.5 mg, 77%. $^1$H NMR 300 MHZ d$^6$-DMSO δ (ppm): 11.15 (s, 1H, OH); 9.40 (bs, 1H, H1', NH$_{indole}$); 7.22 (d, 1H, H7', $^3$J=8.60 Hz); 6.94 (s, 2H, ArH); 6.69 (bs, 1H); 6.49 (d, 1H, H2,$^3$J=8.05 Hz); 6.44 (d, 1H, H1, $^3$J=8.2 Hz); 5.46 (s, 1H, H5β); 4.13 (m, 1H); 3.38–3.22 (m, 3H); 3.06–2.95 (m, 3H); 2.64–2.47 (m, 3H); 1.74 (m, 1H); 0.68–0.59 (m, 1H); 0.53–0.48 (m, 1H, CHcyclo-C$_3$H$_5$); 0.43–0.40 (m, 1H, CHcyclo-C$_3$H$_5$). IR KBr disc ν (cm$^{-1}$): 3328.9 (bs); 3221.4 (bs); 2926.3 (bs); 2180.7 (s, CN); 1633.9 (s); 1567.2 (s); 1560 (s); 1490 (m); 1459(m); 1385.6(w); 1352.2(w); 1154.2(w); 1115.1(m). HRFABMS MNOBA matrix for C$_{28}$H$_{28}$N$_6$O$_3$: Calculated 497.2256, found 497.2297 [M+H]$^+$. CHN analysis calculated C (67.73); H (5.68); N (16.92). found C (67.35); H (5.67); N (16.53).

The intermediate compound (24) was prepared as follows.

a. 5'-N'-Cyano-N-[17-(cyclopropylmethyl)-6,7-didehydro-4,5α-epoxy-3,14-dihydroxyindolo[2',3':6,7]morphinian]-O-phenyl isourea (24)

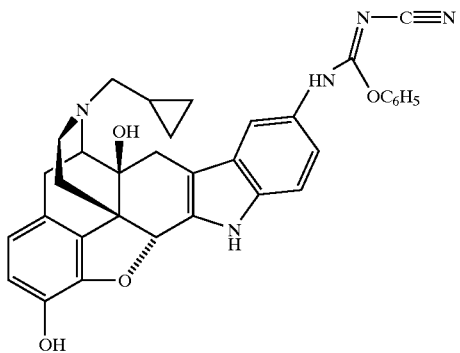

5'-Aminonalrindole (6) (n=0) (896.6 mg, 2.09 mmol) was dissolved in methyl alcohol (150 ml).

N-Cyanodiphenylcarbonimidate (9) (1 equiv., 497 mg, 2.09 mmol) was added and the solution was heated at 60° C. for 24 hours under nitrogen. After this time the reaction vessel was cooled to room temperature and all volatiles were removed in vacuo. The resultant brown oil was subjected to flash column chromatography to afford the title isourea as a white amorphous foam. Yield: 82%, 1.7 mol, 981 mg. $^1$H NMR 300 MHz CDCl$_3$ δ (ppm): 11.13 (bs, 1H); 8.98 (bs, 1H); 7.43–7.12 (m, 7H, ArH); 6.76 (m, 1H); 6.50 (m, 2H, H1&H2); 5.51 (s, 1H, H5); 3.36–2.02 (m, 11H); 1.58 (m, 1H); 0.87 (m, 1H); 0.54–0.52 (m, 2H); 0.14–0.12 (m, 2H). $^{13}$C NMR d6-DMSO 75.48 MHZ δ (ppm): 157.78; 143.49; 141.25; 140.34; 135.60; 131.65; 131.20; 130.22; 129.83; 127.83; 126.48; 124.57; 123.92; 121.62; 119.25; 118.84; 117.44; 115.68; 111.90; 110.63; 84.12; 72.65; 62.05; 60.73; 60.24; 58.97; 47.71; 43.93; 31.40; 29.15; 23.17; 21.24; 14.56; 9.47; 4.41; 3.92. HR-FABMS MNOBA matrix for C$_{34}$H$_{31}$N$_5$O$_4$: Calculated [M+H]$^+$ 574.6611, Found [M+H]$^+$ 574.2493. IR KBr disc ν (cm$^{-1}$): 3334.2 (s); 3080.6 (bw); 2925.6 (bw); 2841.1 (bw); 2192.9 (s, CN); 1728.0 (m); 1622.3 (s); 1495.5 (m); 1467.3 (m); 1425.1 (m); 1319.4 (m); 1220.6 (m); 1150.3 (m); 1115.1 (m); 1058.8 (w); 960.14 (w); 903.78 (w); 861.5 (w); 798.11 (m); 755.84 (w); 685.40 (w).

5'-Aminonaltrindole (6) (n=0) can be prepared by the methods as described herein above in Example 1.

EXAMPLE 6

5'-N-Cyano-N'-[3-(dimethylaminopropyl)]-N"-[17-(cyclopropylmethyl)6,7-didehydro4,5α-epoxy-3,14-dihydroxyindolo[2',3':6,7]morphinian]-guanidine (20)

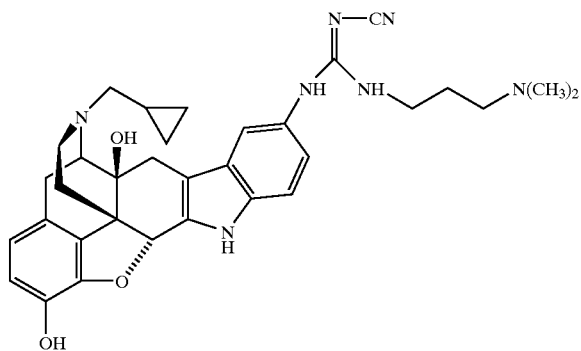

O-Phenyl isourea (24) (100 mg, 0.17 mmol) and 3-dimethylaminopropylamine (1 equiv., 0.175 mmol, 22 μl) in methyl alcohol (3 ml) were heated for 24 hours at 60° C. as described in Example 5. The title compound was purified by flash column chromatography [CHCl$_3$:MeOH:NH$_3$, 9:90:1]. Yield: 56%, 57 mg, 0.098 mmol. White amorphous solid. $^1$H NMR 300 MHz d$^6$-DMSO δ_(ppm): 11.22 (s, 1H, O$\underline{H}$); 8.91 (bs, 1H, H1', N$\underline{H}_{indole}$); 7.28 (d, 1H, H7', $^3$J=8.51 Hz); 7.13 (s, 1H, H4'); 6.87 (dd, 1H, $^3$J=8.60 Hz, $^4$J=2.01 Hz); 6.46 (m, 1H, H2&H1); 5.50 (s, 1H, H5β); 4.72 (bs, 1H); 3.20 (m, 1H); 3.04 (m, 1H); 2.72–2.02 (m, 17H); 1.64 (m, 8H); 0.87 (m, 1H); 0.48 (m, 2H, C$\underline{H}$cyclo-C$_3$H$_5$); 0.12 (m, 2H, C$\underline{H}$cyclo-C$_3$H$_5$). IR KBr disc ν (cm$^{-1}$): 3416.4 (bs); 2931.2 (m); 2818.7 (m); 2172.6 (s, CN); 1567.2 (s); 1454.7 (s); 1328.1 (w); 1152.2 (m); 1117.2 (w); 1060.9 (w); 948.4 (w); 906.25 (w); 871.09 9 (w); 800.78 (m); 667.2 (m). HRFABMS MNOBA matrix for C$_{33}$H$_{39}$N$_7$O$_3$: calculated: 582.7281, found 582.3201[M+H]$^+$. CHN analysis calculated C (68.14); H (6.76); N (16.85). found C (68.31); H (6.78); N (16.72).

O-Phenyl isourea (24) can be prepared by the methods as described herein above in Example 5.

EXAMPLE 7

5'-N-Cyano-N'-[2-(1-aminoethylpyrrolidine)]-N"-[17-(cyclopropylmethyl)-6,7-didehydro4,5α-epoxy-3,14dihydroxyindolo[2',3':6,7]morphinian]-guanidine (21)

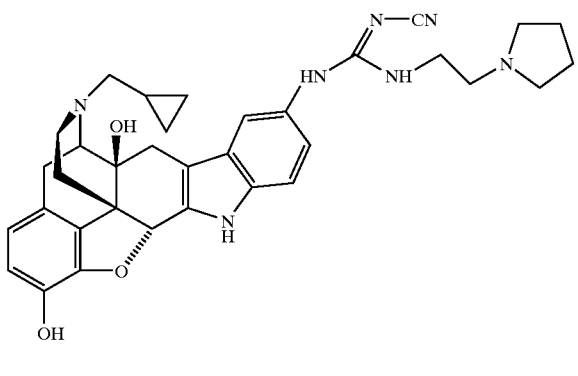

O-Phenylisourea (24) (0.201 mmol, 115 mg) was dissolved in methanol (3 ml). 1-(2-Aminoethyl)-pyrrolidine (1 equiv., 23 mg, 0.026 ml, 0.201 ml) was added and the reaction vessel was sealed and heated at 60° C. for 96 hours. Volatile components were removed in vacuo and the resultant clear oil was dissolved in a minimum amount of ethyl acetate and triturated with hexanes. This afforded the title compound as an off white crystalline solid. Flash column chromatography [SiO$_2$, EtOAc:MeOH:NH$_3$] gave (21) as a white amorphous foam. Yield: 89 mg, 0.143 mmol, 71%. $^1$H NMR 300 MHz d$^6$-DMSO δ_(ppm): 11.23 (s, 1H, O$\underline{H}$); 9.47 (bs, 1H, H1', N$\underline{H}_{indole}$); 7.26 (d, 1H, H7', $^3$J=8.70 Hz); 7.15 (d, 1H, H4', $^4$J=1.74 Hz); 6.87 (dd, 1H, $^3$J=8.60 Hz, $^4$J=2Hz); 6.48 (d, 1H, H2, $^3$J=8.05 Hz); 6.44 (d, 1H, H1, $^3$J=8.2 Hz); 5.48 (s, 1H, H5β); 3.20 (m, 1H); 3.04 (m, 1H); 2.72–2.02 (m, 15H); 1.64 (m, 8H); 0.87 (m, 1H); 0.48 (m, 2H, C$\underline{H}$cyclo-C$_3$H$_5$); 0.12 (m, 2H, C$\underline{H}$cyclo-C$_3$H$_5$). IR KBr disc ν (cm$^{-1}$): 3416.4 (bs); 2931.2 (m); 2818.7 (m); 2171.9 (s, CN); 1567.2 (s); 1454.7 (s); 1328.1 (w); 1152.2 (m); 1117.2 (w); 1060.9 (w); 948.4 (w); 906.25 (w); 871.09 9w); 800.78 (m); 667.2 (m). HRFABMS MNOBA matrix for C$_{34}$H$_{39}$N$_7$O$_3$: calculated 594.3196, found 594.3193 [M+H]$^+$. CHN analysis calculated C (68.78); H (6.62); N (16.51). found C (68.7); H (6.57); N (16.43).

O-Phenyl isourea (24) can be prepared by the methods as described herein above in Example 5.

EXAMPLE 8

The following illustrate representative pharmaceutical dosage forms, containing a compound of formula I ('Compound X'), for therapeutic or prophylactic use in humans.

| (I) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula (I):

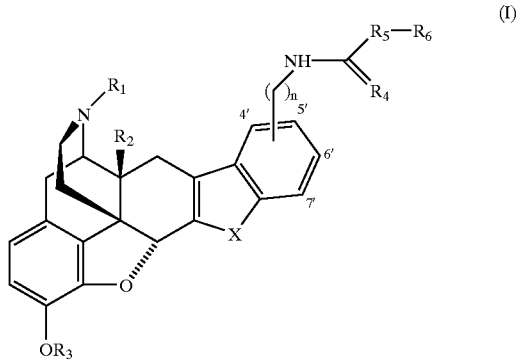

wherein
$R_1$ is $(C_1-C_6)$alkyl, $(C_2-C_6)$alkenyl, $(C_2-C_6)$alkynyl, $(C_3-C_7)$cycloalkyl, $(C_5-C_7)$cycloalkenyl, $(C_3-C_6)$ cycloalkyl$(C_1-C_6)$alkyl, $(C_5-C_7)$cycloalkenyl$(C_1-C_6)$ alkyl, aryl, heteroaryl, aryl$(C_1-C_6)$alkyl, or heteroaryl $(C_1-C_6)$alkyl;

$R_2$ is H, OH, $(C_1-C_6)$alkoxy, $(C_1-C_6)$alkanoyloxy, $NR_aR_b$ or $SR_c$;

$R_3$ is H, aryl$(C_1-C_6)$alkyl, $(C_1-C_6)$alkyl, $(C_1-C_6)$ alkanoyl, or $(C_1-C_6)$alkylC(=S);

$R_4$ is =O, =S, or =$NR_d$;

$R_d$ is H, CN, $CONH_2$, $COCF_3$, $(C_1-C_6)$alkanoyl, $(C_1-C_6)$ alkyl, or $(CH_2)_pNR_eR_f$; or $R_d$ together with $R_6$ is —$(CH_2)_q$— and forms a ring;

p is 1,2,3, or4;

$R_5$ is $NR_m$;

$R_6$ is H, $(C_1-C_6)$alkyl, $(C_3-C_7)$Cycloalkyl, aryl, heteroaryl, aryl$(C_1-C_6)$alkyl, heteroaryl$(C_1-C_6)$alkyl, $NR_gR_h(C_1-C_6)$alkyl, or C(=$NR_j$)$NHR_k$; or when $R_4$ is =$NR_d$, $R_6$ together with $R_d$ is —$(CH_2)_q$— and forms a ring;

q is 2 or 3;

X is O, S, or NY;

Y is H, $(C_1-C_6)$alkyl, or aryl$(C_1-C_6)$alkyl;

n is 0,1,2,3, or4;

$R_a$—$R_c$ and $R_d$—$R_f$ are each independently H, $(C_1-C_6)$ alkyl, $(C_1-C_6)$alkanoyl, or —C(=S)$(C_1-C_6)$alkyl;

$R_g$ and $R_h$ are each independently H, $(C_1-C_6)$alkyl, $(C_1-C_6)$alkanoyl, —C(=NH)$NR_aR_b$, or —C(=S) $(C_1-C_6)$alkyl, or $R_g$ and $R_d$ together with the nitrogen to which they are attached are pyrrolidino, piperidino or morpholino;

$R_j$ and $R_k$ are each independently H, $(C_1-C_6)$alkyl, $(C_2-C_6)$alkenyl, $(C_2-C_6)$alkynyl, $(C_3-C_7)$Cycloalkyl, $(C_3-C_7)$cycloalkyl$(C_1-C_6)$alkyl, $(C_5-C_7)$ Cycloalkenylalkyl, aryl, heteroaryl, aryl$(C_1-C_6)$alkyl, or heteroaryl$(C_1-C_6)$alkyl; and $R_m$ is hydrogen or $(C_1-C_6)$alkyl;

or a pharmaceutically acceptable salt thereof;

provided that $R_d$ is not $(C_1-C_6)$alkyl when n is 1, $R_4$ is NH, and $R_5$ is NH, wherein any heteroaryl is a radical attached via a ring carbon of a monocyclic ring containing five or six ring atoms consisting of carbon atoms and one N(X) heteroatom wherein X is absent or is H, O, $(C_1-C_4)$alkyl, phenyl or benzyl, or consisting of carbon atoms and a heteroatom selected from the group consisting of non-peroxide oxygen, and sulfur.

2. The compound of claim 1 wherein $R_1$ is $(C_2-C_6)$ alkenyl or $(C_3-C_6)$cycloalkyl$(C_1-C_6)$alkyl.

3. The compound of claim 1 wherein $R_1$ is cyclopropylmethyl or allyl.

4. The compound of claim 1 wherein $R_2$ is OH.

5. The compound of claim 1 wherein $R_3$ is H.

6. The compound of claim 1 wherein $R_4$ is $=NR_d$.

7. The compound of claim 1 wherein $R_4$ is $=NH$ or $=NCN$.

8. The compound of claim 1 wherein $R_5$ is NH.

9. The compound of claim 1 wherein $R_6$ is H.

10. The compound of claim 1 wherein $R_6$ is hydrogen, ethyl, n-butyl, 3-(dimethylamino)propyl, or 2-pyrrolidinoethyl.

11. The compound of claim 1 wherein $R_6$ is $C(=N_j)NHR_k$.

12. The compound of claim 1 wherein $R_d$, together with $R_6$, is $—(CH_2)_q—$ and forms a ring.

13. The compound of claim 1 wherein $R_m$ is hydrogen.

14. The compound of claim 1 wherein n is 0.

15. The compound of claim 1 wherein n is 1.

16. The compound of claim 1 wherein the group

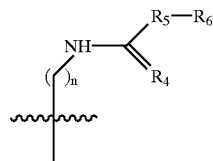

is substituted at the 5' position of the formula (I) ring system.

17. The compound of claim 1 wherein X is NH.

18. A pharmaceutical composition comprising a compound of claim 1, in combination with a pharmaceutically acceptable diluent or carrier.

19. A therapeutic method for preventing or treating a pathological condition or symptom in a mammal wherein kappa receptor activity is implicated and antagonism of kappa receptors is desired comprising administering to the mammal an effective amount of a compound of claim 16.

20. The method of claim 19 wherein the mammal is a human.

21. The method of claim 19 wherein the condition is psychosis, or paralysis due to ischemic spinal cord injury.

22. A therapeutic method for suppressing appetite in a mammal in need of such treatment comprising administering to the mammal an effective amount of a compound of claim 16.

* * * * *

UNITED STATES PATENT AND TRADEMARK OFFICE
CERTIFICATE OF CORRECTION

PATENT NO. : 6,500,824 B1
DATED : December 31, 2002
INVENTOR(S) : Philip S. Portoghese Ph.D and Robert M. Jones It is certified that error appears in the above-identified patent and that said Letters Patent is hereby corrected as shown below:

<u>Title page,</u>
Item [56], below "Assistant Examiner—Raymond Covington", insert the following:
-- *Attorney, Agent, or Firm*—Schwegman, Lundberg, Woessner & Kluth, P.A. --.

<u>Column 1,</u>
Line 11, delete "#da01533" and insert -- # da01533 --, therefor.

<u>Column 26,</u>
Line 40, delete "—$CH_2)_q$—" and insert -- —$(CH_2)_q$— --, therefor.

Signed and Sealed this

Twenty-fourth Day of June, 2003

JAMES E. ROGAN
*Director of the United States Patent and Trademark Office*